US011798150B2

United States Patent
Yin et al.

(10) Patent No.: US 11,798,150 B2
(45) Date of Patent: Oct. 24, 2023

(54) SUPER-RESOLUTION RECONSTRUCTION PREPROCESSING METHOD AND SUPER-RESOLUTION RECONSTRUCTION METHOD FOR CONTRAST-ENHANCED ULTRASOUND IMAGES

(71) Applicant: Nanjing Transcend Vivoscope Bio-Technology Co., LTD, Nanjing (CN)

(72) Inventors: Jingyi Yin, Nanjing (CN); Jue Zhang, Nanjing (CN)

(73) Assignee: Nanjing Transcend Vivoscope Bio-Technology Co., LTD, Nanjing (CN)

( * ) Notice: Subject to any disclaimer, the term of this patent is extended or adjusted under 35 U.S.C. 154(b) by 0 days.

(21) Appl. No.: 17/837,973

(22) Filed: Jun. 10, 2022

(65) Prior Publication Data
US 2022/0301132 A1    Sep. 22, 2022

Related U.S. Application Data

(63) Continuation of application No. PCT/CN2021/093327, filed on May 12, 2021.

(30) Foreign Application Priority Data

May 18, 2020    (CN) .......................... 202010419625.7

(51) Int. Cl.
G06T 5/50       (2006.01)
G06T 7/68       (2017.01)
(Continued)

(52) U.S. Cl.
CPC ............... G06T 5/50 (2013.01); G06T 5/002 (2013.01); G06T 7/30 (2017.01); G06T 7/68 (2017.01);
(Continued)

(58) Field of Classification Search
CPC .. G06T 5/50; G06T 5/002; G06T 7/30; G06T 7/68; G06T 2207/10132;
(Continued)

(56) References Cited

U.S. PATENT DOCUMENTS 7,744,534 B2    6/2010  Chalana et al.
11,116,474 B2 *  9/2021  Ebbini ................. A61B 8/5223
(Continued)

FOREIGN PATENT DOCUMENTS

CN       103876776 A       6/2014
CN       107361791 A  *   11/2017  ............... A61B 8/06
(Continued)

OTHER PUBLICATIONS

International Search Report issued in corresponding PCT Application No. PCT/CN2021/093327, dated Aug. 12, 2021.

*Primary Examiner* — Tom Y Lu
*Assistant Examiner* — Pardis Sohraby
(74) *Attorney, Agent, or Firm* — Westbridge IP LLC

(57) ABSTRACT

A super-resolution reconstruction preprocessing method of contrast-enhanced ultrasound images includes: acquiring an image set to be preprocessed; acquiring grayscale fluctuation signal of a pixel point in the registered contrast-enhanced ultrasound images to be preprocessed; performing denoise reconstruction operation on the image set to be preprocessed to obtain a reconstructed feature parameter image, and performing interpolation calculation on the reconstructed feature parameter image to obtain a sparse microbubble image. By analyzing the grayscale fluctuation signals of the collocated pixel point set in the plurality of frames of the registered contrast-enhanced ultrasound images to be preprocessed, a signal-to-noise ratio and a signal-to-background ratio are improved. By performing interpolation operation on the reconstructed feature parameter image,
(Continued)

spatial decoupling of overlapping microbubbles is realized, and influence of strong noise and high concentration microbubble on the accuracy of super-resolution reconstruction is reduced.

19 Claims, 8 Drawing Sheets

(51) Int. Cl.
  *G06T 7/30* (2017.01)
  *G06T 5/00* (2006.01)
(52) U.S. Cl.
  CPC ............... *G06T 2207/10132* (2013.01); *G06T 2207/20212* (2013.01); *G06T 2207/30104* (2013.01)
(58) Field of Classification Search
  CPC . G06T 2207/20212; G06T 2207/30104; G06T 3/4053; A61B 8/06; A61B 8/481; A61B 8/5223; A61B 8/5269
  USPC .......................................................... 382/299
  See application file for complete search history.

(56) References Cited

U.S. PATENT DOCUMENTS

| | | | | |
|---|---|---|---|---|
| 2014/0153793 | A1* | 6/2014 | Goharrizi | G06T 5/004 382/128 |
| 2015/0201895 | A1* | 7/2015 | Suzuki | G06T 5/50 382/131 |
| 2017/0039706 | A1* | 2/2017 | Mikhno | G06T 11/003 |
| 2017/0071574 | A1* | 3/2017 | Zhu | A61B 8/5207 |
| 2020/0234446 | A1* | 7/2020 | Mischi | G16H 50/50 |
| 2021/0321988 | A1* | 10/2021 | Ji | A61B 8/5269 |
| 2022/0071596 | A1* | 3/2022 | Wang | A61B 8/0891 |

FOREIGN PATENT DOCUMENTS

| | | | | |
|---|---|---|---|---|
| CN | 107361791 A | | 11/2017 | |
| CN | 109215093 A | | 1/2019 | |
| CN | 110740688 A | * | 1/2020 | ............... A61B 8/06 |
| CN | 111598965 A | | 8/2020 | |
| WO | WO-2019073227 A1 | * | 4/2019 | ............... A61B 8/06 |
| WO | WO-2020081915 A1 | * | 4/2020 | ........... A61B 8/0891 |
| WO | WO-2020097298 A1 | * | 5/2020 | ......... G01N 29/0654 |

* cited by examiner

SUPER-RESOLUTION RECONSTRUCTION PREPROCESSING METHOD AND SUPER-RESOLUTION RECONSTRUCTION METHOD FOR CONTRAST-ENHANCED ULTRASOUND IMAGES

CROSS-REFERENCE TO RELATED APPLICATIONS

The present application is a continuation of International Application No. PCT/CN2021/093327, filed on May 12, 2021, which claims priority to Chinese Patent Application No. 202010419625.7, filed on May 18, 2020. All applications are incorporated herein by reference in their entireties.

TECHNICAL FIELD

Embodiments of the present application relate to the field of ultrasound imaging technology, and in particular to a super-resolution reconstruction preprocessing method of contrast-enhanced ultrasound images, a super-resolution reconstruction method, a super-resolution reconstruction preprocessing device, a super-resolution reconstruction apparatus, an electronic device, and a non-transitory computer readable storage medium.

BACKGROUND

Ultrasound localization microscopy (ULM), as a kind of microvasculature imaging technology, overcomes influence of acoustic diffraction limit and achieves super-resolution imaging of microvessels. At present, high-concentration microbubbles that may shorten acquisition time are often used in clinical application. However, high-concentration microbubbles tend to overlap, which affects accuracy of microbubble localization in ULM. In a process of the clinical acquisition, interference of strong noise and a tissue background signal could not be avoided, and thus the accuracy of microbubble localization is affected. Limited by existing clinical acquisition conditions, it is impossible to reconstruct a super-resolution image of the microvasculature quickly, efficiently and accurately, which brings a great challenge to the clinical application of the current ultrasound super-resolution imaging techniques.

SUMMARY

In view of this, embodiments of the present application provide a super-resolution reconstruction preprocessing method of contrast-enhanced ultrasound images, a super-resolution reconstruction method, a super-resolution reconstruction preprocessing device, a super-resolution reconstruction apparatus, an electronic device, and a non-transitory computer readable storage medium, in order to solve a problem that a ultrasound super-resolution image of microvasculature could not be reconstructed quickly, efficiently and accurately due to the limitation of clinical acquisition conditions in the prior art.

According to an aspect of the present application, an embodiment of the application provides a super-resolution reconstruction preprocessing method of contrast-enhanced ultrasound images. The super-resolution reconstruction preprocessing method of contrast-enhanced ultrasound images includes: acquiring an image set to be preprocessed, the image set to be preprocessed including a plurality of frames of registered contrast-enhanced ultrasound images to be preprocessed; acquiring grayscale fluctuation signals of pixel points in the registered contrast-enhanced ultrasound images to be preprocessed; performing denoising and reconstruction operation on the grayscale fluctuation signals of the collocated pixel point set to obtain a reconstructed feature parameter image based on grayscale fluctuation signals of a collocated pixel point set and the collocated pixel point set includes a plurality of collocated pixel points located at a same pixel coordinate in different frames of the registered contrast-enhanced ultrasound images to be preprocessed; and performing interpolation calculation on the reconstructed feature parameter image to obtain a sparse microbubble image based on the grayscale fluctuation signals of the collocated pixel point set and grayscale fluctuation signals of an associated pixel point set associated with the collocated pixel point set, the associated pixel point set including a plurality of associated pixel points, the associated pixel point is adjacent to the collocated pixel point in a same frame of the registered contrast-enhanced ultrasound image to be preprocessed and the plurality of associated pixel points are located at a same pixel coordinate in different frames of the registered contrast-enhanced ultrasound images to be preprocessed.

According to an aspect of the present application, an embodiment of the application provides a super-resolution reconstruction method of contrast-enhanced ultrasound images, including: selecting at least one image set to be preprocessed from contrast-enhanced ultrasound images; performing preprocessing operation on the at least one image set to be preprocessed respectively to obtain at least one frame of sparse microbubble image, a method of the preprocessing operation adopting any one of the above-mentioned super-resolution reconstruction preprocessing method; acquiring pixel values and estimated degree of radial symmetry of pixel points in the sparse microbubble image; performing weighted calculation on the pixel values and estimated degree of radial symmetry of the corresponding pixel points located in the same frame of sparse microbubble image to obtain at least one frame of local super-resolution image respectively corresponding to the at least one frame of the sparse microbubble image; and superimposing the at least one frame of the local super-resolution image to obtain a reconstructed super-resolution image.

According to another aspect of the present application, an embodiment of the application provides a super-resolution reconstruction preprocessing device of contrast-enhanced ultrasound images including a first preprocessing acquisition module, configured to acquire an image set to be preprocessed, the image set to be preprocessed including a plurality of frames of registered contrast-enhanced ultrasound images to be preprocessed; a grayscale fluctuation signal acquisition module, configured to acquire grayscale fluctuation signals of pixel points in the registered contrast-enhanced ultrasound image to be preprocessed; a denoising enhancement reconstruction module, configured to perform denoising and reconstruction operation on the grayscale fluctuation signals of the collocated pixel point set to obtain a reconstructed feature parameter image based on grayscale fluctuation signals of a collocated pixel point set, the collocated pixel point set including a plurality of collocated pixel points located at a same pixel coordinate in different registered contrast-enhanced ultrasound images to be preprocessed; and, a sparse microbubble image reconstruction module, configured to perform interpolation calculation on the reconstructed feature parameter image to obtain a sparse microbubble image based on the grayscale fluctuation signals of the collocated pixel point set and grayscale fluctuation signals of an associated pixel point set associated with the collocated pixel point set, the associated pixel point set including a plurality of associated pixel points, and the associated pixel points being adjacent to the collocated pixel point in a same frame of the registered contrast-enhanced ultrasound images to be preprocessed, and the plurality of associated pixel points being located at a same pixel coordinate in different frames of the registered contrast-enhanced ultrasound images to be preprocessed.

According to another aspect of the present application, an embodiment of the application provides a super-resolution reconstruction apparatus of a contrast-enhanced ultrasound images, including: a first selection module, configured to select at least one image set to be preprocessed from contrast-enhanced ultrasound data; a preprocessing apparatus, configured to perform preprocessing operation on the at least one image set to be preprocessed respectively to obtain at least one sparse microbubble image, adopting the super-resolution reconstruction preprocessing method according to any one of the above-mentioned super-resolution reconstruction preprocessing method; an microbubble trajectory highlighting module, configured to acquire pixel values and estimated degree of radial symmetry of pixel points in the sparse microbubble image; and perform weighted calculation on the pixel values and the estimated degree of radial symmetry of the pixel points located in the same frame of the sparse microbubble image to obtain at least one frame of local super-resolution image respectively corresponding to the at least one frame of the sparse microbubble image; and a superimposition module, configured to superimpose the at least one frame of the local super-resolution image to obtain a reconstructed super-resolution image.

According to another aspect of the present application, an embodiment of the application provides an electronic device, the electronic device including: a processor; a memory, computer program instruction being stored in the memory. The processor is configured to execute any one of the above-mentioned super-resolution reconstruction preprocessing method, or any one of the above-mentioned super-resolution reconstruction method.

According to another aspect of the present application, an embodiment of the application provides a non-transitory computer readable storage medium. The non-transitory computer readable storage medium stores a computer program instruction for a processor executing any one of the above-mentioned super-resolution reconstruction preprocessing method, or any one of the above-mentioned super-resolution reconstruction method.

Embodiments of the present application provide the super-resolution reconstruction preprocessing method, the super-resolution reconstruction method, the super-resolution reconstruction preprocessing device, the super-resolution reconstruction apparatus, the electronic device, and the computer readable storage medium of a contrast-enhanced ultrasound image. By analyzing the grayscale fluctuation signals of the collocated pixel point set in the plurality of frames of the registered contrast-enhanced ultrasound images to be preprocessed, microbubble signals of the image set to be preprocessed in a current time window are distinguished from a noise or background signals, and a signal-to-noise ratio and a signal-to-background ratio are improved, and the reconstructed feature parameter image with a microbubble signal enhancement to eliminate background noise signal. By calculating the similarity of the grayscale fluctuation signals of the collocated pixel point set and the grayscale fluctuation signal of the associated pixel point set associated with the collocated pixel point set, the interpolation made in the reconstructed feature parameter image may separate different overlapping microbubbles, therefore spatial decoupling of overlapping microbubbles is realized, and microbubbles overlapping caused by acoustic diffraction limit is solved. By performing preprocessing operation on the image set to be preprocessed, influence of high concentration microbubbles and strong noise on the accuracy of super-resolution imaging may be effectively reduced. By performing weighted calculation on the pixel values and the estimated degree of radial symmetry of the pixel points located in each frame of the sparse microbubble image, a point spread function (PSF) of the microbubble points is slimmed, a deformation information of the s along microbubble trajectories is retained, an trajectory skeleton of the microbubble motion along vessels in each frame of the sparse microbubble image becomes clearer, a non-localization-based motion of the microbubbles is enhanced along microbubble trajectories, a track information of the microbubbles along the moving directions is retained, and local super-resolution images are obtained and finally integrated into a complete ultrasound super-resolution reconstruction image of the microvasculature. Different from the traditional sparse microbubble localization and accumulation strategy, the non-localization-based trajectories enhancement method retains the trajectory skeleton of the moving microbubbles, thereby spatial resolution and reconstruction speed of the super-resolution reconstruction are greatly improved, and the reconstruction of the super-resolution image is realized fast and efficiently.

DETAILED DESCRIPTION OF THE EMBODIMENTS

Figure 1:
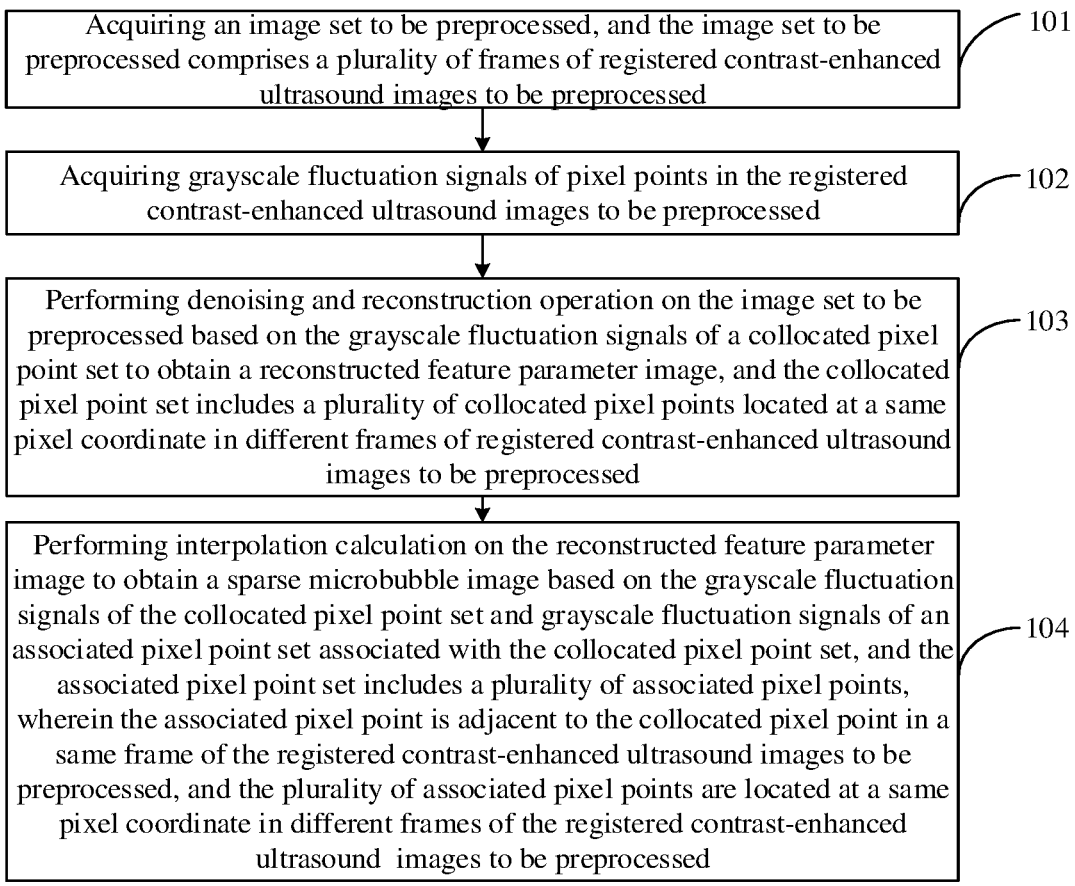
FIG. 1 is a flowchart of a super-resolution reconstruction preprocessing method of a contrast-enhanced ultrasound image according to an embodiment of the present application.

The technical scheme in embodiments of the application will be clearly and completely described below with reference to accompanying drawings in the embodiments of the application. Obviously, the described embodiments are only part of the embodiments of the application, not all of the embodiments. Based on the embodiments in the application, all other embodiments obtained by those skilled in the art without creative work fall within the protection scope of this application.

Application Overview

Microvasculature imaging is of great benefit to diagnosis of diseases. Ultrasound microbubble contrast agent invented by Gramiak in the 1970s makes contrast-enhanced ultrasound imaging of small vessels possible. Microbubbles flow in blood vessels and vibrate in an ultrasound beam, producing harmonic signals during resonance, which can be selectively detected by the microbubble-specific software available, so that the blood vessels be distinguished from a background tissue signal with high sensitivity in deeper tissues. At present, contrast-enhanced ultrasound (CEUS) imaging has been used as a commonly employed technique for the routine blood flow imaging in many clinical diagnosis processes, but it is still limited by diffraction limit and cannot achieve high spatial resolution imaging of microvasculature (i.e., vessel diameter is smaller than 100 μm).

Errico et al. proposed an ultrasound microvasculature imaging technology based on contrast-enhanced ultrasound imaging, i.e., ultrasound localization microscopy (ULM). By detecting, isolating, locating and accumulating isolated microbubbles, acoustic diffraction limit is broken, and the super-resolution imaging of the microvasculature with diameters of tens of microns is realized.

However, in ultrasound super-resolution imaging based on ULM, strong noise may easily induce false localizations. Microbubble signals detected in deep tissue are easy to be disturbed by tissue signals, so it is difficult to distinguish the background or the noise signal, which affects accuracy of microbubble localization. However, the current clinical conditions cannot meet the prerequisites above. Secondly, in order to realize accurate localization of the microbubbles, ultrasound localization microscopy needs to maintain low concentration microbubbles in the blood flow. However, at present, in order to meet clinical guidelines for perfusion practice, high concentration microbubbles are commonly used in the clinic. However, due to the fact that overlapped microbubbles are frequently observed under high microbubble concentrations, it is unable to guarantee the accuracy of microbubble localization, which will affect accuracy of microvasculature imaging.

At present, there is an urgent need for new super-resolution reconstruction methods of contrast-enhanced ultrasound images, which may quickly achieve microvasculature imaging under the conditions of high microbubble concentrations and strong noise that are common in the clinical application, so that ultrasound super-resolution imaging may be widely used in the clinical application.

In view of the above-mentioned technical problems, the basic principles of the present application are to propose a super-resolution reconstruction preprocessing method of the contrast-enhanced ultrasound images. By analyzing grayscale fluctuation signals of the collocated pixel point set in the plurality of frames of registered contrast-enhanced ultrasound images to be preprocessed within a time scale, the microbubble signals are distinguished from the background and the noise signals. By calculating the similarity of the grayscale fluctuation signal of the collocated pixel point set and grayscale fluctuation signals of grayscale fluctuation signals of the associated pixel point set associated with the collocated pixel point set, a reconstructed feature parameter images are interpolated, an efficient decoupling of spatially overlapping microbubbles is achieved, therefore influences of the high concentration microbubbles and the strong noise on the accuracy of super-resolution imaging are effectively reduced. By selecting the image set to be preprocessed within the same time window for preprocessing, the trajectories of microbubbles along vessels is enhanced in the moving directions by the estimated degree of radial symmetry of the pixel points, and the trajectory skeletons of microbubbles are retained, thereby the spatial resolution and reconstruction speed of the super-resolution reconstruction process are greatly improved, and the reconstruction of the microvasculature is realized fast and efficiently.

After introducing the basic principles of the present application, various non-limiting embodiments of the present application will be described in detail below with reference to the accompanying drawings.

Exemplary Preprocessing Method

FIG. 1 is a flowchart of a super-resolution reconstruction preprocessing method of contrast-enhanced ultrasound images according to an embodiment of the present application. As shown in FIG. 1, the super-resolution reconstruction preprocessing method includes the followed steps.

Step 101: acquiring an image set to be preprocessed, and the image set to be preprocessed includes a plurality of frames of the registered contrast-enhanced ultrasound images to be preprocessed.

A target to be imaged is injected with ultrasound contrast agents, and an ultrasound probe is used to detect an area to be imaged. When contrast-enhanced signals appear, contrast-enhanced ultrasound images are collected. The plurality of frames of the contrast-enhanced ultrasound images are registered to suppress image deformation caused by movement of the probe or breath, in order to obtain a plurality of frames of registered images, i.e., a plurality of frames of the registered contrast-enhanced ultrasound images. Some registered contrast-enhanced ultrasound images are selected from the plurality of frames of the registered contrast-enhanced ultrasound images as registered contrast-enhanced ultrasound images to be preprocessed. Therefore, each frame of the registered contrast-enhanced ultrasound image to be preprocessed is a registered image.

A ultrasound frequency to collect the plurality of frames of the contrast-enhanced ultrasound images may be 30 Hz or 50 Hz. The frequency of collecting the plurality of frames of the contrast-enhanced ultrasound images only needs to meet specific clinical acquisition conditions, and the frequency of collecting the plurality of frames of the contrast-enhanced ultrasound images is not specifically limited in embodiments of the present application. A selection method of selecting part from the plurality of frames of the registered contrast-enhanced ultrasound images may be to select 4 images at an interval of 1; or select 3 images at an interval of 2; or select 5 images at an interval of 1. The specific selection method of selecting part from the plurality of frames of the registered contrast-enhanced ultrasound images in the embodiments of the application is not limited.

A registration method for the plurality of frames of the contrast-enhanced ultrasound images may be to use a Morphon multi-scale registration method to deal with the plurality of frames of the contrast-enhanced ultrasound images, and the specific method of the registration is not limited in the embodiments of the present application. The injection method of the ultrasound contrast agent maybe as followed. Sulfur hexafluoride microbubble freeze-dried powder Sonovue 59 mg is dissolved in 5 mL of 0.9% sodium chloride solution to prepare the ultrasound contrast agent, and 0.2 mL was injected into the model containing 3 L of sodium chloride solution at one time, or injected continuously at a rate of 0.2-5.0 µL/min. The specific types of ultrasound contrast agents and specific injection methods are not limited in the embodiments of the present application.

Step 102: acquiring the grayscale fluctuation signals of a pixel points in the registered contrast-enhanced ultrasound image to be preprocessed.

Based on an ultrasound equipment that collects contrast-enhanced ultrasound images, each frame of the contrast-enhanced ultrasound image has divided pixel coordinates, and the pixel coordinates have pixel points. Since the plurality of frames of the contrast-enhanced ultrasound images are collected by a same equipment and each frame of the contrast-enhanced ultrasound images is registered with same registered parameters, pixel coordinate division on each frame of the contrast-enhanced ultrasound images is the same, and pixel coordinate division on each frame of the registered contrast-enhanced ultrasound image to be preprocessed is also the same. The grayscale fluctuation of each pixel point of the each frame of the registered contrast-enhanced ultrasound images to be preprocessed is acquired. The grayscale fluctuation signal is used for representing change of the grayscale fluctuation of a current pixel point in a current frame of the registered contrast-enhanced ultrasound image.

As long as the grayscale fluctuation signal of each pixel point can be obtained, a specific acquisition method of the grayscale fluctuation signal is not limited in the embodiments of the application.

Step 103: performing denoising and reconstruction operation on the grayscale fluctuation signal of the collocated pixel point set to obtain a reconstructed feature parameter image based on the grayscale fluctuation signal of a collocated pixel point set, the collocated pixel point set including a plurality of collocated pixel points located at a same pixel coordinate in different frames of the registered contrast-enhanced ultrasound images to be preprocessed.

Since the pixel coordinate division on each frame of the registered contrast-enhanced ultrasound images to be preprocessed is the same, there are also the same pixel coordinates on each frame of the registered contrast-enhanced ultrasound image to be preprocessed in a image set to be preprocessed. Pixel points located at the same pixel coordinate in the different frames of the registered contrast-enhanced ultrasound images to be preprocessed are the collocated pixel points. In each frame of the registered contrast-enhanced ultrasound images to be preprocessed, the grayscale fluctuation signal of the pixel point is a one-dimensional signal, i.e., the grayscale fluctuation signal of each collocated pixel point is a one-dimensional grayscale fluctuation signal. The grayscale fluctuation signal of the collocated pixel point set located at the same pixel coordinate in different frames of the registered contrast-enhanced ultrasound images to be preprocessed is a one-dimensional signal, i.e., one collocated pixel point set is a one-dimensional grayscale fluctuation signal. The one-dimensional grayscale fluctuation signal is used for reflecting periodicity and randomness of the grayscale fluctuation of the image set to be preprocessed located in a current time window. Since the characteristics and distributions of the grayscale fluctuation signals of microbubble signals and background or noise signals are different, the microbubble grayscale fluctuation signal has stronger periodicity and stronger randomness. Based on the one-dimensional grayscale fluctuation signals of a plurality of the collocated pixel points, the microbubble signals may be distinguished from the noise or background signals, which enhances the microbubble signals and weakens the background or noise signals, and finally the reconstructed feature parameter images with highlighted microbubble signals and diminished background or noise signals are obtained.

For example, an image set to be preprocessed within a 5-frame time window includes five consecutive frames of the contrast-enhanced ultrasound images to be preprocessed of A, B, C, D, and E. Located at the pixel coordinate (1, 1) of the contrast-enhanced ultrasound image of frame A to be preprocessed is a pixel point a. Located at the pixel coordinate (1, 1) of the contrast-enhanced ultrasound image of frame B to be preprocessed is a pixel point b. Located at the pixel coordinate (1, 1) of the contrast-enhanced ultrasound image of frame C to be preprocessed is a pixel point c. Located at the pixel coordinate (1, 1) of the contrast-enhanced ultrasound image of frame D to be preprocessed is a pixel point d. Located at the pixel coordinate (1, 1) of the contrast-enhanced ultrasound image of frame E to be preprocessed is a pixel point e. Then the pixel point a, the pixel point b, the pixel point c, the pixel point d and the pixel point e are the collocated pixel point set. Based on a 1-multiplied-5-dimensional grayscale fluctuation signal that is composed of the pixel point a, the pixel point b, the pixel point c, the pixel point d and the pixel point e, the microbubble signal can be distinguished from the noise or the background signal in the image set to be preprocessed in the current time window, and a signal-to-noise ratio and a signal-to-background ratio are improved.

A quantity of the collocated pixel points in the image set to be preprocessed is the same as a quantity of the same pixel coordinates. The quantity of the same pixel coordinates in the image set to be preprocessed is determined by the equipment collecting the contrast-enhanced ultrasound image.

Step 104: performing pixel interpolation on the reconstructed feature parameter image to obtain a sparse microbubble image based on the grayscale fluctuation signal of the collocated pixel point set and grayscale fluctuation signal of an associated pixel point set associated with the collocated pixel point set, the associated pixel point set including a plurality of associated pixel points which are adjacent to the collocated pixel point in a same frame of the registered contrast-enhanced ultrasound image to be preprocessed and located at a same pixel coordinate in different frames of the registered contrast-enhanced ultrasound images to be preprocessed.

Diffraction occurs when a size of the microbubbles is smaller than the ultrasound wavelength, which makes a spatial resolution of ultrasound imaging lower than a half wavelength. This phenomenon is called acoustic diffraction limit. Due to the diffraction limit, the microbubbles will overlap on each frame of the registered contrast-enhanced ultrasound images to be preprocessed. Pixels belonging to a same microbubble have almost same grayscale fluctuation signals and have high similarity to each other, while pixels belonging to different microbubbles have completely different grayscale fluctuation signals and have low similarity to each other. Therefore, performing interpolation operation on the reconstructed feature parameter image based on the grayscale fluctuation signal of the collocated pixel point set and the grayscale fluctuation signals of the associated pixel point set associated with the collocated pixel point set plays a role of separating and isolating different microbubbles.

Each associated pixel point in the associated pixel point set is also located at the same pixel coordinate in different frames of the registered contrast-enhanced ultrasound images to be preprocessed, that is to say, the associated pixel point set itself is also one the collocated pixel point set. Only relative to the selected associated pixel point set, each pixel point of the associated pixel point set and each collocated pixel point of the current collocated pixel point set are adjacent and have the same relative position in the same frame of the contrast-enhanced ultrasound image to be preprocessed. The grayscale fluctuation signal of the collocated pixel point is a one-dimensional grayscale fluctuation signal. The selected current collocated pixel point set is a one-dimensional grayscale fluctuation signal. Each associated pixel point is a one-dimensional grayscale fluctuation signal. The associated pixel point set is also a one-dimensional grayscale fluctuation signal. The associated pixel point set is a one-dimensional grayscale fluctuation signal located near the current pixel point set. Using the similarity of two one-dimensional grayscale fluctuation signals to interpolate the reconstructed feature parameter image can separate different adjacent microbubbles.

For example, located at the pixel coordinate (1, 1) of the registered contrast-enhanced ultrasound image of frame A to be preprocessed is the pixel point a. Located at the pixel coordinate (0, 1) of the registered contrast-enhanced ultrasound image of frame A to be preprocessed is a pixel a1. Located at the pixel coordinate (1, 2) of the registered contrast-enhanced ultrasound image of frame A to be preprocessed is a pixel point a2. Located at the pixel coordinate (1, 1) of the registered contrast-enhanced ultrasound image of frame B to be preprocessed is the pixel point b. Located at the pixel coordinate (0, 1) of the registered contrast-enhanced ultrasound image of frame B to be preprocessed is a pixel point b1. Located at the pixel coordinate (1, 2) of the registered contrast-enhanced ultrasound image of frame B to be preprocessed is a pixel point b2. Located at the pixel coordinate (1, 1) of the registered contrast-enhanced ultrasound image of frame C to be preprocessed is the pixel point c. Located at the pixel coordinate (0, 1) of the registered contrast-enhanced ultrasound image of frame C to be preprocessed is a pixel point c1. Located at the pixel coordinate (1, 2) of the registered contrast-enhanced ultrasound image of frame C to be preprocessed is a pixel point c2. Located at the pixel coordinate (1, 1) of the registered contrast-enhanced ultrasound image of frame D to be preprocessed is the pixel point d. Located at the pixel coordinate (0, 1) of the registered contrast-enhanced ultrasound image of frame D to be preprocessed is a pixel point d1. Located at the pixel coordinate (1, 2) of the registered contrast-enhanced ultrasound image of frame D to be preprocessed is a pixel point d2. Located at the pixel coordinate (1, 1) of the registered contrast-enhanced ultrasound image of frame E to be preprocessed is the pixel point e. Located at the pixel coordinate (0, 1) of the registered contrast-enhanced ultrasound image of frame E to be preprocessed is a pixel point e1. Located at the pixel coordinate (1, 2) of the contrast-enhanced ultrasound image of frame E to be preprocessed is a pixel point e2. Then the pixel point a, the pixel point b, the pixel point c, the pixel point d and the pixel point e are the current collocated pixel point set, the pixel point a1, the pixel point b1, the pixel point c1, the pixel point d1 and the pixel point e1 are the associated pixel point set, and the pixel point a2, the pixel point b2, the pixel point c2, the pixel point d2 and the pixel point e2 are also the associated pixel point set.

The quantity of the associated pixel point sets corresponding to each collocated pixel point set may be 4, 6, 8, 10, and 12, and the embodiment of the present application does not specifically limit the quantity of the associated pixel point sets corresponding to each collocated pixel point set.

In the embodiment of the present application, by analyzing the grayscale fluctuation signal of the collocated pixel point set in the plurality of frames of the registered contrast-enhanced ultrasound images to be preprocessed, a noise signal or a background signal of the image set to be preprocessed in the current time window are distinguished, a signal-to-noise ratio and a signal-to-background ratio are improved, and the reconstructed feature parameter image with enhanced microbubble signals and weakened background and noise signals is obtained. By calculating the similarity of the grayscale fluctuation signals of the collocated pixel point set and the grayscale fluctuation signals of the associated pixel point set associated with the collocated pixel point set, the interpolation is made in the reconstructed feature parameter image to separate different microbubbles, spatial decoupling of overlapping microbubbles is realized, and the diffraction limit is broken.

In an embodiment of the present application, the grayscale fluctuation signal is a kind of signal formed by arranging pixel values of the pixel points in time sequence, and the grayscale fluctuation signal of the collocated pixel point set is a kind of one-dimensional signal formed by arranging pixel values of the plurality of collocated pixel points in the collocated pixel point set in time sequence. There are differences in the characteristics of the grayscale fluctuation signals among the microbubbles and the background or the noise, i.e., the periodicity of microbubbles and the background or the noise. The periodicity of microbubble signal is stronger and the distribution of microbubble signal is more random. Characteristics of the grayscale fluctuation signal includes a randomness of the grayscale fluctuation distribution and a periodicity of the grayscale fluctuation. Then the microbubble signal can be distinguished from the background or the noise signal by using the characteristic of the grayscale fluctuation distribution and the characteristic of the grayscale fluctuation randomness of the collocated pixel points. The spatial decoupling of the overlapping microbubbles can be realized by performing interpolation operation using the similarity between the one-dimensional signal formed by the collocated pixel point set and the one-dimensional signal formed by surrounding pixel point sets.

Figure 2:
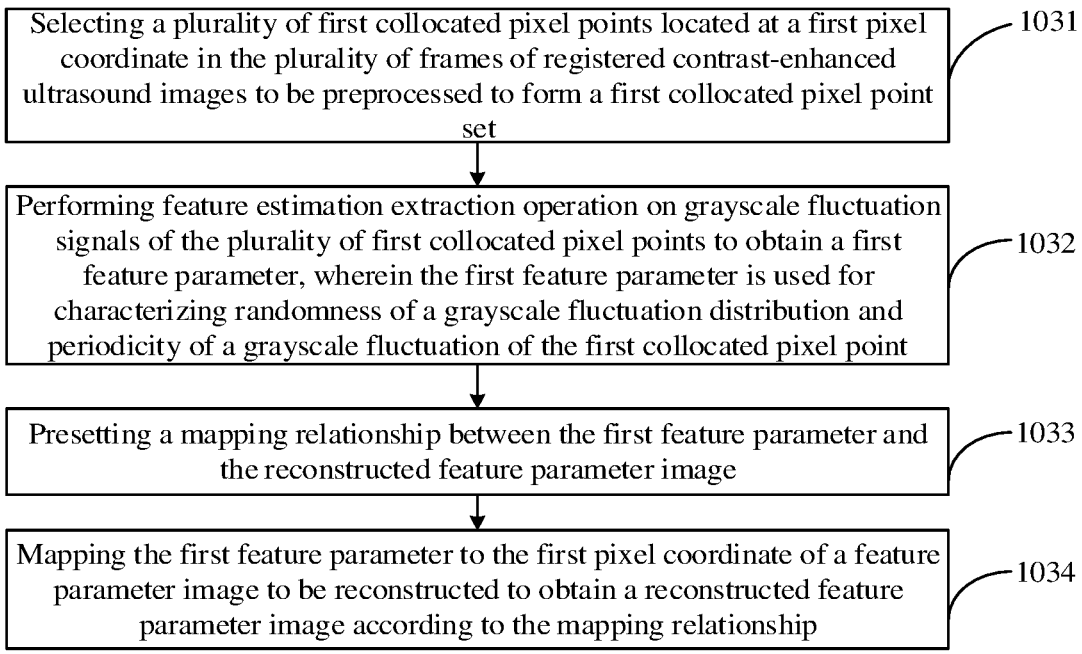
FIG. 2 is a flowchart of obtaining a reconstructed feature parameter image of a super-resolution reconstruction preprocessing method of a contrast-enhanced ultrasound image according to an embodiment of the present application.

FIG. 2 is a flowchart of obtaining a reconstructed feature parameter image of a super-resolution reconstruction preprocessing method of contrast-enhanced ultrasound images according to an embodiment of the present application. As shown in FIG. 2, the performing denoising and reconstruction operation on the grayscale fluctuation signals of the collocated pixel point set to obtain a reconstructed feature parameter image based on grayscale fluctuation signals of a collocated pixel point set specifically includes the following steps.

Step 1031: selecting a plurality of first collocated pixel points located at a first pixel coordinate in the plurality of frames of the registered contrast-enhanced ultrasound images to be preprocessed to form a first collocated pixel point set.

The first collocated pixel point at the first pixel coordinate of each frame of the registered contrast-enhanced ultrasound images to be preprocessed is selected to form the first collocated pixel point set. For example, the pixel point a, b, c, d and e, locating in the pixel coordinate (1, 1) of each frame in the five consecutive frames of the registered contrast-enhanced ultrasound images to be preprocessed of A, B, C, D, and E, form the first collocated pixel point set.

The first pixel coordinate is only a reference. The first pixel coordinate may be any pixel coordinate in the image set to be preprocessed. The specific selection of the first pixel coordinate is not limited in the embodiments of the present application.

Step 1032: performing feature estimation extraction operation on grayscale fluctuation signals of a plurality of first collocated pixel points to obtain a first feature parameter, the first feature parameter being used for characterizing randomness of a grayscale fluctuation distribution and periodicity of a grayscale fluctuation of the first collocated pixel point.

The first feature parameter extraction is performed on the plurality of first collocated pixel points, and the first feature parameter is used for characterizing the randomness of the grayscale fluctuation distribution of the plurality of collocated pixel points. The randomness of grayscale fluctuation signal of pixel points belonging to the microbubbles is higher, and the randomness of grayscale fluctuation signal of pixel points belonging to the noise or the background is lower. The first feature parameter is used for characterizing the periodicity of grayscale fluctuation of the plurality of collocated pixel points. The periodicity of grayscale fluctuation of pixel points belonging to the microbubbles is stronger, and the periodicity of grayscale fluctuation of pixel points belonging to the noise and background is lower, that is, the periodicity of grayscale fluctuation of pixel points belonging to the noise and the background is weaker. Each pixel point set at each pixel coordinate in the image to be preprocessed is traversed to extract the first feature parameters corresponding to each collocated pixel point. The plurality of the first feature parameters are used to reflect the characteristics of the grayscale fluctuation distribution and the grayscale fluctuation periodicity of the entire image set to be preprocessed.

Step 1033: presetting a mapping relationship between the first feature parameter and the reconstructed feature parameter image.

Since the plurality of the first feature parameters reflect the grayscale fluctuation distribution characteristic and grayscale fluctuation periodicity characteristic of the entire image set to be preprocessed, and the periodicity and distribution of the grayscale fluctuation signal corresponding to microbubbles and the background or the noise are different, the grayscale fluctuation distribution characteristic and grayscale fluctuation periodicity characteristic can be used to distinguish the microbubble signal from the background signal or the noise signal. Thereby, according to the first feature parameter, the microbubble signal can be distinguished from the background signal or noise signal. The mapping relationship between the first feature parameter and the reconstructed feature parameter image is preset. According to the mapping relationship between the extracted first feature parameter and the reconstructed feature parameter image, the reconstructed feature parameter image with the enhanced microbubble signals and weakened background or the noise signals can be reconstructed.

For example, if a value of the first feature parameter preset in advance is large, it is indicated that the grayscale fluctuation periodicity of the corresponding collocated pixel point set is stronger, and the probability that each collocated pixel point belongs to the microbubble is bigger, and then the gray value of the pixel point in the corresponding feature parameter image to be reconstructed is higher. If the value of the first feature parameter preset in advance is small, it is indicated that the grayscale fluctuation periodicity of the corresponding collocated pixel point set is weaker, and the probability that each collocated pixel point belongs to the background or the noise is bigger, and then the gray value of the pixel point in the corresponding feature parameter image to be reconstructed is lower. As long as the mapping relationship between the first feature parameter and the reconstructed feature parameter image is preset in advance, the reconstructed feature parameter image with the enhanced microbubble signals and weakened background or the noise signals may be reconstructed. The specific implementation manner of the presetting mapping relationship is not limited in the embodiments of the present application.

Step 1034: mapping the first feature parameter to the first pixel coordinate of a feature parameter image to be reconstructed to obtain the reconstructed feature parameter image according to the mapping relationship.

The reconstructed feature parameter image is a reconstructed image with the enhanced microbubble signals and weakened background or the noise signals (i.e., the signal-to-noise ratio and the signal-to-background ratio are improved), based on the grayscale fluctuation distribution characteristic and the grayscale fluctuation periodicity characteristic reflected by the first feature parameter of the image set to be preprocessed. The first feature parameter is corresponding to the first pixel coordinate of the feature parameter image to be reconstructed. According to the mapping relationship, it is accurately conveyed through an alignment of the coordinates that the microbubble signal needs to be enhanced and the background signal needs to be weakened and most of the background and noise interference are removed.

In the embodiment of the present application, by extracting the plurality of the first feature parameters reflecting the grayscale fluctuation distribution characteristic and the grayscale fluctuation periodicity characteristic of the entire image set to be preprocessed, the microbubble signal is distinguished from the background or noise signal. Using the preset mapping relationship between the first feature parameter and the reconstructed feature parameter image, the situation, that the signal in the microbubble area needs to be enhanced and the signal in the background area needs to be weakened, is accurately conveyed to the corresponding location of the feature parameter image to be reconstructed through the coordinates. The reconstructed feature parameter image with improved signal-to-noise ratio and signal-to-background ratio is obtained.

In an embodiment of the present application, a method of feature estimation extraction operation includes: an auto-correlation estimation calculation or an information entropy estimation calculation. The periodicity strength of the grayscale fluctuation signal of each collocated pixel point is measured by the auto-correlation estimation; and the randomness of the distribution of the grayscale fluctuation signal of each collocated pixel point is measured by the information entropy estimation. The first feature parameter is obtained by the auto-correlation estimation calculation or the information entropy estimation calculation. Using the plurality of first characteristic parameters that reflects the grayscale fluctuation distribution characteristic and the grayscale fluctuation periodicity characteristic of the entire image set to be preprocessed, the microbubble signal is distinguished from the noise signal or the background signal in the image set to be preprocessed in the current time window, and the signal-to-noise ratio and the signal-to-background ratio are improved, and the reconstructed image with the enhanced microbubble signals and weakened background or the noise signals is obtained.

Figure 3:
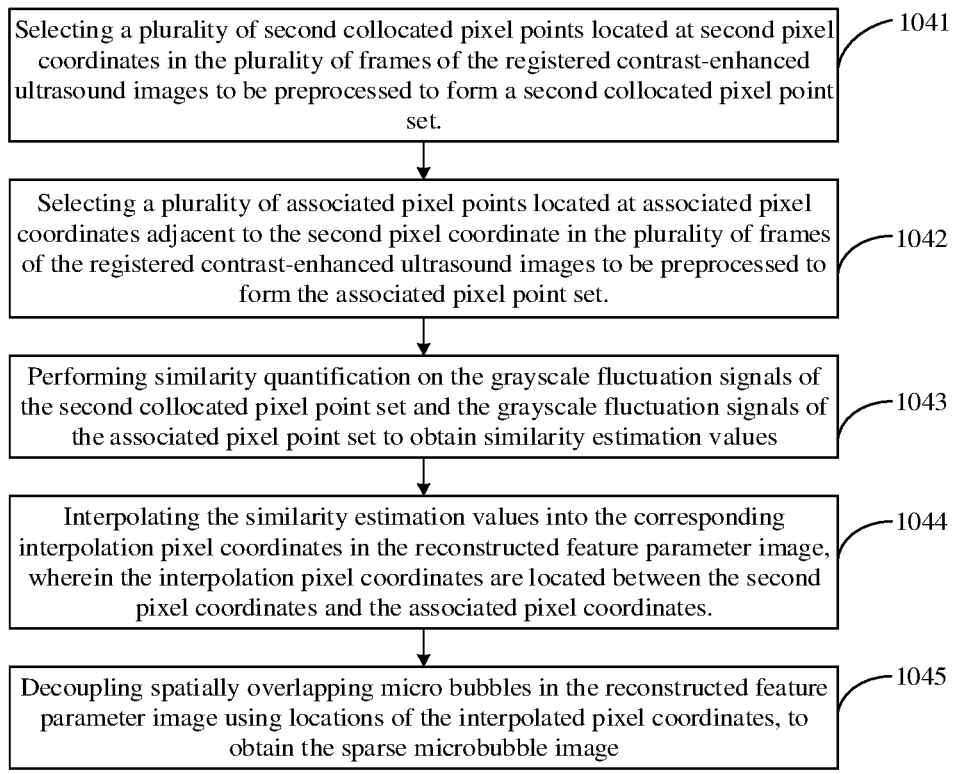
FIG. 3 is a flowchart of interpolation calculation to obtain a sparse microbubble image of a super-resolution reconstruction preprocessing method of contrast-enhanced ultrasound images according to an embodiment of the present application.

FIG. 3 is a flowchart of interpolation calculation to obtain a sparse microbubble image of a super-resolution reconstruction preprocessing method of a contrast-enhanced ultrasound image according to an embodiment of the present application. As shown in FIG. 3, the performing interpolation calculation on the reconstructed feature parameter image to obtain a sparse microbubble image based on the grayscale fluctuation signals of the collocated pixel point set and grayscale fluctuation signals of an associated pixel point set associated with the collocated pixel point set, includes the following steps.

Step 1041: selecting a plurality of second collocated pixel points located at a second pixel coordinate in the plurality of frames of the registered contrast-enhanced ultrasound images to be preprocessed to form a second collocated pixel point set.

The second collocated pixel point at the second pixel coordinate of each frame of the registered contrast-enhanced ultrasound images to be preprocessed are selected to form the second collocated pixel point set. For example, the pixel points a, b, c, d and e, locating in the pixel coordinate (1, 1) of each frame of the registered contrast-enhanced ultrasound images to be preprocessed A, B, C, D, and E, form the second collocated pixel point set.

The second pixel coordinate is just a reference, which may be any pixel coordinate point in the image set to be preprocessed. The second pixel coordinate may be the same coordinate as the first pixel coordinate, or may not be the same coordinate as the first pixel coordinate. The specific selection of the second pixel coordinate is not limited in the embodiment of the present application.

Step 1042: selecting a plurality of associated pixel points located at associated pixel coordinates adjacent to the second pixel coordinate in the plurality of frames of the registered contrast-enhanced ultrasound images to be preprocessed to form the associated pixel point set.

In each frame of the registered contrast-enhanced ultrasound image, the plurality of associated pixel points located at the associated pixel coordinates adjacent to the second pixel coordinates are selected. There is more than one associated pixel coordinate corresponding to the second pixel coordinate, and there is more than one associated pixel point set corresponding to each collocated pixel point set. The embodiments of the present application do not specifically limit the quantity of the associated pixel point set corresponding to each the collocated pixel point set. In the following, taking the example that there are four adjacent associated pixel coordinates of the second pixel coordinate, that is, the four associated pixel point sets corresponding to the collocated pixel point set. For example, the associated pixel coordinates of the plurality of pixel coordinate (1, 1) of the registered contrast-enhanced ultrasound image of frame A to be preprocessed are (0, 1), (1, 2), (2, 1), and (1, 0), and the associated pixel points of the second pixel point a are a1, a2, a3 and a4 separately located at (0, 1), (1, 2), (2, 1) and (1, 0). Similarly, in the registered contrast-enhanced ultrasound images of frame B to be preprocessed, the associated pixel points of the second pixel point b are b1, b2, b3 and b4. In the registered contrast-enhanced ultrasound image of frame C to be preprocessed, the associated pixel points of the second pixel point c are c1, c2, c3 and c4. In the registered contrast-enhanced ultrasound image of frame D to be preprocessed, the associated pixel points of the second pixel point d are d1, d2, d3 and d4. In the registered contrast-enhanced ultrasound image of frame E to be preprocessed, the associated pixel points of the second pixel point e are e1, e2, e3 and e4. Then a, b, c, d, and e form the collocated pixel point set, a1, b1, c1, d1 and e1 form an associated pixel point set, a2, b2, c2, d2 and e2 form an associated pixel point set, a3, b3, c3, d3 and e3 form an associated pixel point set, and a4, b4, c4, d4 and e4 form an associated pixel point set. The collocated pixel point set (a, b, c, d and e) is a 1-times-5-dimensional grayscale fluctuation signal. Similarly, the associated pixel point set (a1, b1, c1, d1 and e1), (a2, b2, c2, d2 and e2), (a3, b3, c3, d3 and e3) and (a4, b4, c4, d4 and e4) are all 1-times-5-dimensional grayscale fluctuation signals.

Step 1043: performing similarity quantification on the grayscale fluctuation signals of the second collocated pixel point set and the grayscale fluctuation signals of the associated pixel point set to obtain similarity estimation values.

The similarity calculation is run by using the grayscale fluctuation signal of the second collocated pixel point and the associated pixel points associated with the second collocated pixel points in each frame of the contrast-enhanced ultrasound images to be preprocessed (the grayscale fluctuation signals of the second collocated pixel point set and the associated pixel points), i.e., the similarity of two one-dimensional grayscale fluctuation signals is quantified, thereby the similarity of the two signals becomes a more intuitive similarity estimation.

Step 1044: interpolating the similarity estimation values into the corresponding interpolation pixel coordinates in the reconstructed feature parameter image, the interpolation pixel coordinates being located between the second pixel coordinates and the associated pixel coordinates.

The similarity estimation value of the second collocated pixel point set and the associated pixel points is interpolated into the corresponding interpolation pixel coordinate in the reconstructed feature parameter image, so that the intuitive similarity estimation value is presented between each pixel in the reconstructed feature parameter image.

For example, the similarity of the collocated pixel point set (a, b, c, d and e) and the associated pixel point set (a1, b1, c1, d1 and e1) is calculated to obtain a similarity estimation value Z1, and the Z1 is interpolated between the pixel coordinates (1, 1) and (0, 1) of the registered contrast-enhanced ultrasound image. And so on, the similarity of the collocated pixel point set (a, b, c, d and e) and the associated pixel point set (a2, b2, c2, d2 and e2) is calculated to obtain a similarity estimation value Z2, and the Z2 is interpolated between the pixel coordinates (1, 1) and (1, 2) of the registered contrast-enhanced ultrasound image. The similarity of the collocated pixel point set (a, b, c, d and e) and the associated pixel point set (a3, b3, c3, d3 and e3) is calculated to obtain a similarity estimation value Z3, and the Z3 is interpolated between the pixel coordinates (1, 1) and (2, 1) of the registered contrast-enhanced ultrasound image. The similarity of the collocated pixel point set (a, b, c, d and e) and the associated pixel point set (a4, b4, c4, d4 and e4) is calculated to obtain a similarity estimation value Z4, and the Z4 is interpolated between the pixel coordinates (1, 1) and (1, 0) of the registered contrast-enhanced ultrasound image Step 1045: decoupling spatially overlapping microbubbles in the reconstructed feature parameter image by using locations of the interpolated pixel coordinates to obtain the sparse microbubble image.

The similarity estimation value is interpolated into the corresponding interpolation pixel coordinate in the reconstructed feature parameter image, so that the intuitive similarity estimation value is presented between each pixel in the reconstructed feature parameter image. The pixels with high similarity belong to the same microbubble, and the pixels with low similarity are separated into different microbubbles. Using interpolation to separate different microbubbles, the spatial decoupling of overlapping microbubbles is realized.

In the embodiment of the application, by calculating the similarity between the grayscale fluctuation signals of the collocated pixel point set and the associated pixel point set, the similarity of the two signals becomes a more intuitive similarity estimation value. The similarity estimation value is interpolated into the corresponding interpolation pixel coordinate in the reconstructed feature parameter image, so that the intuitive similarity estimation value is presented between each pixel in the reconstructed feature parameter image. The pixel points with high similarity belong to the same microbubble, and the pixel points with low similarity are separated into different microbubbles. Using interpolation to separate different microbubbles, the spatial decoupling of overlapping microbubbles is realized, and finally the sparse microbubble image is obtained.

In an embodiment, the method of similarity quantification includes: a cross-entropy estimation or a cross-correlation estimation. The similarity between the two grayscale fluctuation signals of the collocated pixel point set and the associated pixel point set is calculated by the cross-entropy estimation or the cross-correlation estimation, and the similarity of the two signals becomes the more intuitive similarity estimation value. The similarity value is interpolated into the reconstructed feature parameter image, and the overlapping microbubbles are spatially decoupled using the intuitive numerical value, and finally the sparse microbubble image is obtained.

In an embodiment, a quantity of the associated pixel point set is 4. In the plurality of frames of the registered contrast-enhanced ultrasound images to be preprocessed, 4 associated pixel points separately located at 4 associated pixel coordinates adjacent to the second pixel coordinate are selected to form 4 associated pixel point sets corresponding to the collocated pixel point set. The similarity between the collocated pixel point set and each of the four associated pixel point sets is calculated respectively, and the similarity between a pixel point and the surrounding associated pixel points is obtained in more detail, so that the boundary of the overlapping microbubbles is clearer, and the overlapping microbubbles in the reconstructed feature parameter image are spatially decoupled to obtain the sparse microbubble image.

Exemplary Reconstruction Method

Figure 4:
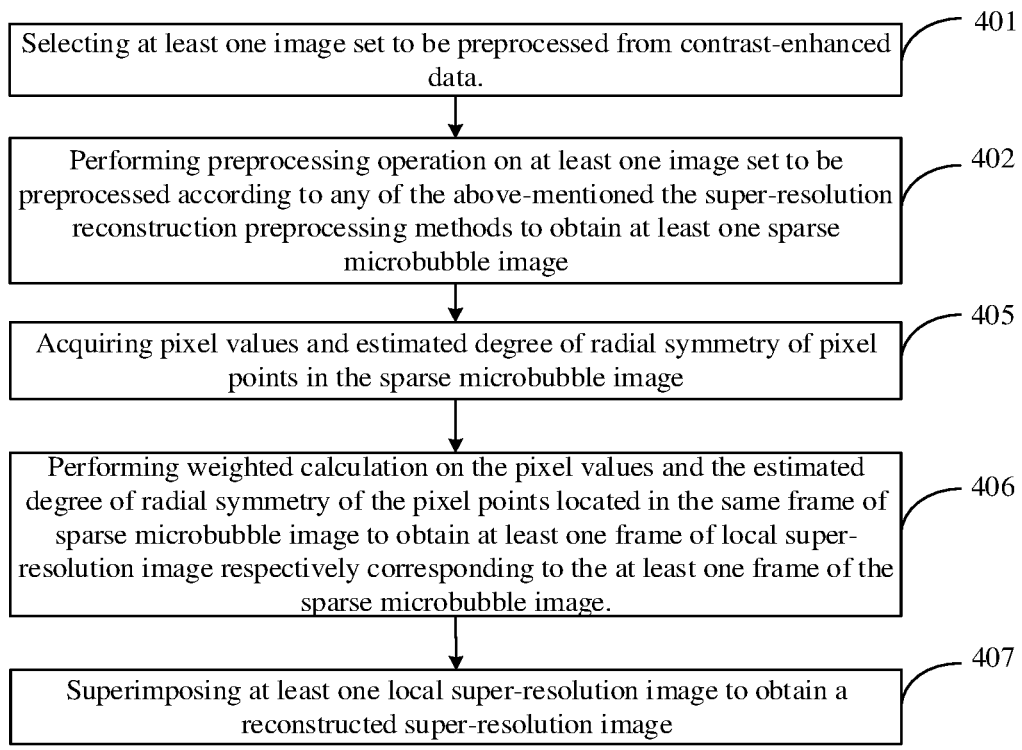
FIG. 4 is a flowchart of a super-resolution reconstruction method of contrast-enhanced ultrasound images according to an embodiment of the present application.

FIG. 4 is a flowchart of a super-resolution reconstruction method of contrast-enhanced ultrasound images according to an embodiment of the present application. As shown in FIG. 4, the super-resolution reconstruction method includes the following steps.

Step 401: selecting at least one image set to be preprocessed from contrast-enhanced data.

The contrast data is a plurality of frames of collected contrast-enhanced ultrasound images. At least one image set to be preprocessed is selected from the plurality of frames of the contrast-enhanced ultrasound images, so that each the image set to be preprocessed is continuous with each other, and microbubbles of each image set to be preprocessed have a stable spatial location within a preset time window. As long as the image set to be preprocessed meets the above conditions, the embodiments of the application do not limit the specific selection method.

Step 402: performing preprocessing operation on the at least one image set to be preprocessed according to any of the above-mentioned the super-resolution reconstruction preprocessing methods to obtain at least one sparse microbubble image.

The image set to be preprocessed is performed preprocessing operation by any of above-mentioned the super-resolution reconstruction preprocessing methods, which effectively reduces the influence of high concentration microbubbles and strong noise on the accuracy of super-resolution imaging. By analyzing the grayscale fluctuation signals of the collocated pixel point set, the microbubble signal is distinguished from the noise or the background signal, and the signal-to-noise ratio and signal-to-background ratio are improved. Performing interpolation calculation on the reconstructed feature parameter image through the similarity of the grayscale fluctuation signals of the collocated pixel point set and the grayscale fluctuation signals of the associated pixel point set associated with the collocated pixel point set, the overlapping microbubbles is spatially decoupled and diffraction limit is broken.

Step 405: acquiring pixel values and estimated degree of radial symmetry of pixel points in the sparse microbubble image.

The radial symmetry refers to the radial symmetry of each pixel point in the local area. Through evaluating a spatial symmetry of a local gradient field of the pixel point, the radial symmetry of each pixel point in the local area is obtained. As long as the estimated degree of radial symmetry of the sparse microbubble image is obtained, the embodiments of the application do not limit the specific algorithm of the estimated degree of radial symmetry.

At least one image set to be preprocessed is performed preprocessing operation respectively to obtain at least one the sparse microbubble image, the pixel value of each pixel point in each sparse microbubble image, and the estimated degree of radial symmetry of each pixel in each sparse microbubble image. Since the microbubbles is elongated along the flowing direction, and the degree of radial symmetry of each pixel in the local area may be obtained by estimating the degree of radial symmetry of the pixel point, then the estimated degree of radial symmetry can retain the deformation information of the microbubbles. Therefore, the estimated degree of radial symmetry of the pixel value of each pixel point is equivalent to retaining the trajectories of the microbubbles.

Step 406: performing weighted calculation on the pixel values and the estimated degree of radial symmetry of the pixel points located in the same frame of the sparse microbubble image to obtain at least one frame of local super-resolution images respectively corresponding to the at least one frame of the sparse microbubble image.

In the actual scene, because the microbubbles are moving, the microbubbles are elongated along the flowing direction. By performing weighted calculation on the pixel values and the estimated degree of radial symmetry of the pixel points, a local super-resolution image in which a central region of the microbubble area is enhanced and an marginal region of the microbubble area is weakened is obtained. By performing weighted calculation on the pixel values and the estimated degree of radial symmetry of the pixel points, a point spread function of the microbubble which is elongated along the microbubble flowing direction is slimmed, therefore the trajectory of the microbubble is retained, and the trajectory skeleton along the moving direction of the microbubble in each frame of the sparse microbubble image becomes clearer, and local super-resolution images are obtained.

Step 407: superimposing at least one frame of the local super-resolution image to obtain a reconstructed super-resolution image.

Each frame of the local super-resolution image is superimposed to form a complete reconstructed ultrasound super-resolution image of microvasculature.

In the embodiment of the application, by performing preprocessing operation on at least one image set to be preprocessed, the influence of high concentration microbubbles and the strong noise on the accuracy of super-resolution imaging may be effectively reduced. By performing weighted calculation on the pixel values and the estimated degree of radial symmetry of the pixel points located in each frame of the sparse microbubble image, the point spread function of the microbubble is slimmed along the moving direction of the microbubble, therefore the deformation information of the microbubble is retained through enhanced trajectory skeletons of microbubbles in each frame of the sparse microbubble image, the track information of the microbubble along the moving direction is retained, and local super-resolution images are obtained. And the local super-resolution images are finally integrated into the complete reconstructed ultrasound super-resolution image of the microvasculature. Different from the traditional ultrasound localization microscopy, the non-localization-based method preserves microbubble trajectories adaptively, thereby spatial resolution and reconstruction speed of ultrasound super-resolution imaging are greatly improved.

Figure 5:
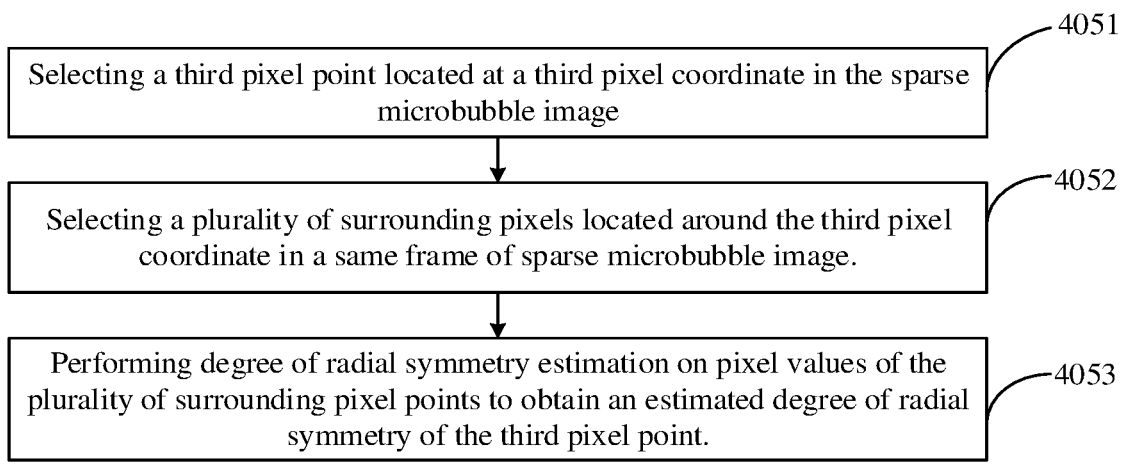
FIG. 5 is a flowchart of the acquiring the estimated degree of radial symmetry of pixel points in a sparse microbubble image of a super-resolution reconstruction preprocessing method of contrast-enhanced ultrasound images according to an embodiment of the present application.

FIG. 5 is a flowchart of the acquiring estimated degree of radial symmetry of pixel points in a sparse microbubble image obtained from a super-resolution reconstruction preprocessing method of contrast-enhanced ultrasound images according to an embodiment of the present application. As shown in FIG. 5, the acquiring the estimated degree of radial symmetry of pixel points in the sparse microbubble image includes the following steps.

Step 4051: selecting a third pixel point located at a third pixel coordinate in the sparse microbubble image.

The third pixel coordinate is only a reference, which may be any pixel coordinate point in the sparse microbubble image, and the specific selection of the third pixel coordinate is not limited in the embodiments of the present application.

Step 4052: selecting a plurality of surrounding pixels located around the third pixel coordinate in a same frame of the sparse microbubble image.

In the same frame of the sparse microbubble image, the plurality of surrounding pixel points around the third pixel are selected. For example, the pixel point a located at the pixel coordinate (1, 1) of the sparse microbubble image of frame A1 and 12 surrounding pixel points around pixel point a are selected. The 12 surrounding pixel points are located on a circle with the pixel point a as the center and a radius of r, and the 12 surrounding pixel points are evenly distributed on the circle.

A quantity of the surrounding pixel points may be 6, 8, 10, 12, 15, 20, etc. The embodiments of the application do not limit the specific quantity of the surrounding pixel points.

Step 4053: performing degree of radial symmetry estimation on pixel values of the plurality of the surrounding pixel points to obtain an estimated degree of radial symmetry of the third pixel point.

The degree of radial symmetry estimation is performed on the pixel value of the pixel point a and the pixel values of 12 surrounding pixel points around the pixel point a to obtain the estimated degree of radial symmetry of the pixel point a.

In the embodiment of the application, by performing degree of radial symmetry estimation on the pixel values of the plurality of the surrounding pixel points around the third pixel coordinate in the same frame of the sparse microbubble image, the deformation information of the microbubble is retained. The estimated degree of radial symmetry of each pixel point on each frame of the sparse microbubble image is obtained through spatial traversal in a preset local area, so that the moving information of the microbubble is enhanced in a non-localization-based way.

In an embodiment, the quantity of the surrounding pixel points is 12, and the radius of degree of radial symmetry is 1.

Figure 6:
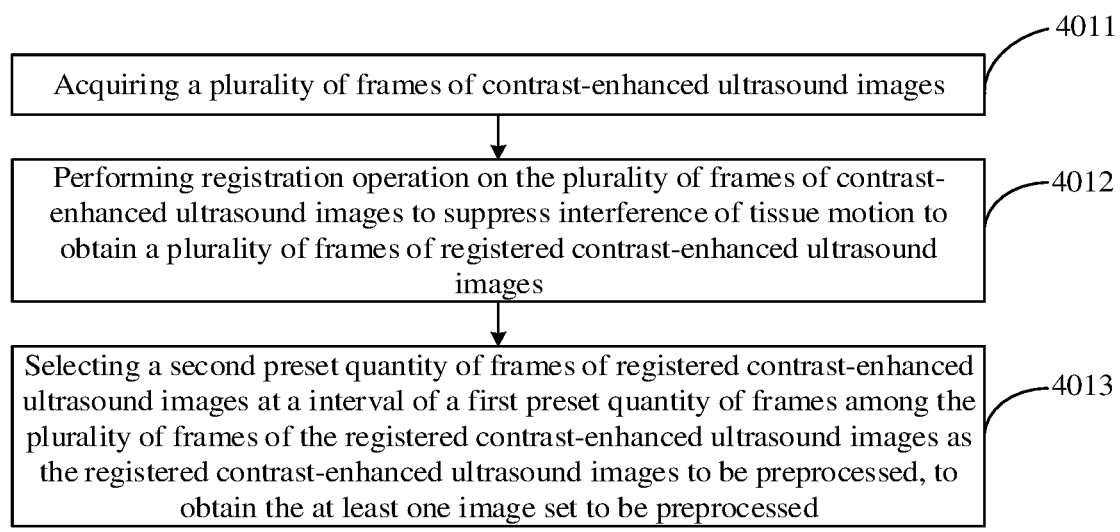
FIG. 6 is a flowchart of the selecting at least one image set to be preprocessed from contrast-enhanced ultrasound images of a super-resolution reconstruction preprocessing method of contrast-enhanced ultrasound images according to an embodiment of the present application.

FIG. 6 is a flowchart of the selecting at least one image set to be preprocessed from contrast-enhanced data of a super-resolution reconstruction preprocessing method of a contrast-enhanced ultrasound image according to an embodiment of the present application. As shown in FIG. 6, the selecting at least one image set to be preprocessed from contrast-enhanced data includes the following steps.

Step 4011: acquiring a plurality of frames of contrast-enhanced ultrasound images.

A target to be imaged is injected with ultrasound contrast agent, and an ultrasound probe is used for detecting an area to be imaged. When a contrast-enhanced ultrasound signal appears, contrast-enhanced ultrasound data is collected to obtain a plurality of frames of the contrast-enhanced ultrasound images.

A frequency of collecting the plurality of frames of the contrast-enhanced ultrasound images may be 30 Hz or 50 Hz. The frequency of collecting the plurality of frames of the contrast-enhanced ultrasound images only needs to meet specific clinical acquisition conditions, and the frequency of collecting the plurality of frames of the contrast-enhanced ultrasound images is not specifically limited in the embodiments of the present application. The acquisition quantity of the plurality of frames of the contrast-enhanced ultrasound images may be 500, 1000, or 1500, etc. The embodiments of the present application do not limit the specific quantity of the plurality of frames of the contrast-enhanced ultrasound images.

Step 4012: performing registration operation on the plurality of frames of the contrast-enhanced ultrasound images to suppress interference of tissue motion, and obtaining a plurality of frames of the registered contrast-enhanced ultrasound images.

The plurality of frames of the contrast-enhanced ultrasound images are registered to suppress image changes caused by the probe and the tissue motion to obtained the plurality of frames of the registered contrast-enhanced ultrasound images. Methods of image registration may be flexible registration and rigid registration, including but not limited to median shift method, scale-invariant feature transformation method, tracking learning detection, optical flow method, and cross-correlation method. Preferably, the tracking learning detection is used for the rigid registration, and the optical flow method is used for the flexible registration. As long as the contrast-enhanced ultrasound images are registered, the embodiments of the present application do not limit the specific method of the registration.

Step 4013: selecting a second preset quantity of frames of the registered contrast-enhanced ultrasound images at a interval of a first preset quantity of frames among the plurality of frames of the registered contrast-enhanced ultrasound images as the registered contrast-enhanced ultrasound images to be preprocessed, to obtain the at least one image set to be preprocessed.

In the plurality of frames of the registered contrast-enhanced ultrasound images, the second preset quantity of frames of the registered contrast-enhanced ultrasound images are selected at every interval of the first preset quantity of frames of the registered contrast-enhanced ultrasound images, i.e., the same time window is selected in the time dimension (the duration of the time window is the second preset quantity). The preprocessing operations such as denoising and reconstruction and interpolation calculation decoupling are performed on the registered contrast-enhanced ultrasound images within the same time window. For example, in N frames of the registered contrast-enhanced ultrasound images, W+1 frames of the registered contrast-enhanced ultrasound images are selected as the registered contrast-enhanced ultrasound images to be preprocessed at every interval of G frames of the registered contrast-enhanced ultrasound images (G is less than W+1, W+1 is less than N), and (NW−1)/G+1 image sets to be preprocessed are formed. Each image set to be preprocessed includes W+1 frames of the registered contrast-enhanced ultrasound images to be preprocessed. The image sets to be preprocessed that are selected from the plurality of frames of the registered contrast-enhanced ultrasound images according to the above-mentioned method are continuous, and the microbubbles of the registered contrast-enhanced ultrasound images to be preprocessed have stable spatial location within a preset time window.

N, G and W are positive integers. The selection method of selecting part from the plurality of frames of the registered contrast-enhanced ultrasound images may be to select 4 frames of images at the interval of 1; or select 3 frames of images at the interval of 1; or select 5 frames of images at the interval of 1. The specific selection method of selecting part from the plurality of frames of the registered contrast-enhanced ultrasound images in the embodiments of the application is not limited.

In the embodiment of the present application, the image set to be preprocessed is obtained by the above-mentioned method, so that the denoising and reconstruction and interpolation calculation are performed within the same time window. So that the microbubbles in each image set to be preprocessed have the stable spatial location within the preset time window, and an effect of fast flow of microbubbles on the super-resolution reconstruction is reduced.

In an embodiment, the first preset quantity is negatively correlated with blood flow velocity; and the second preset quantity is negatively correlated with the blood flow velocity. In an embodiment, the first preset quantity is positively correlated with imaging frame rate; and the second preset quantity is positively correlated with the imaging frame rate.

In order to make the microbubbles have stability of spatial position in a certain time window, the first preset quantity G and the second preset quantity W+1 depend on the microbubble flow velocity and the imaging frame rate. The faster the blood flow velocity, the smaller the values of the first preset quantity G and the first preset quantity W+1. The faster the blood flow velocity, the smaller the values of the first preset quantity G and the first preset quantity W+1. The larger the imaging frame rate, the larger the values of the first preset quantity G and the first preset quantity W+1.

In an embodiment, the first preset quantity is 1; and the second preset quantity is 4.

Figure 7:
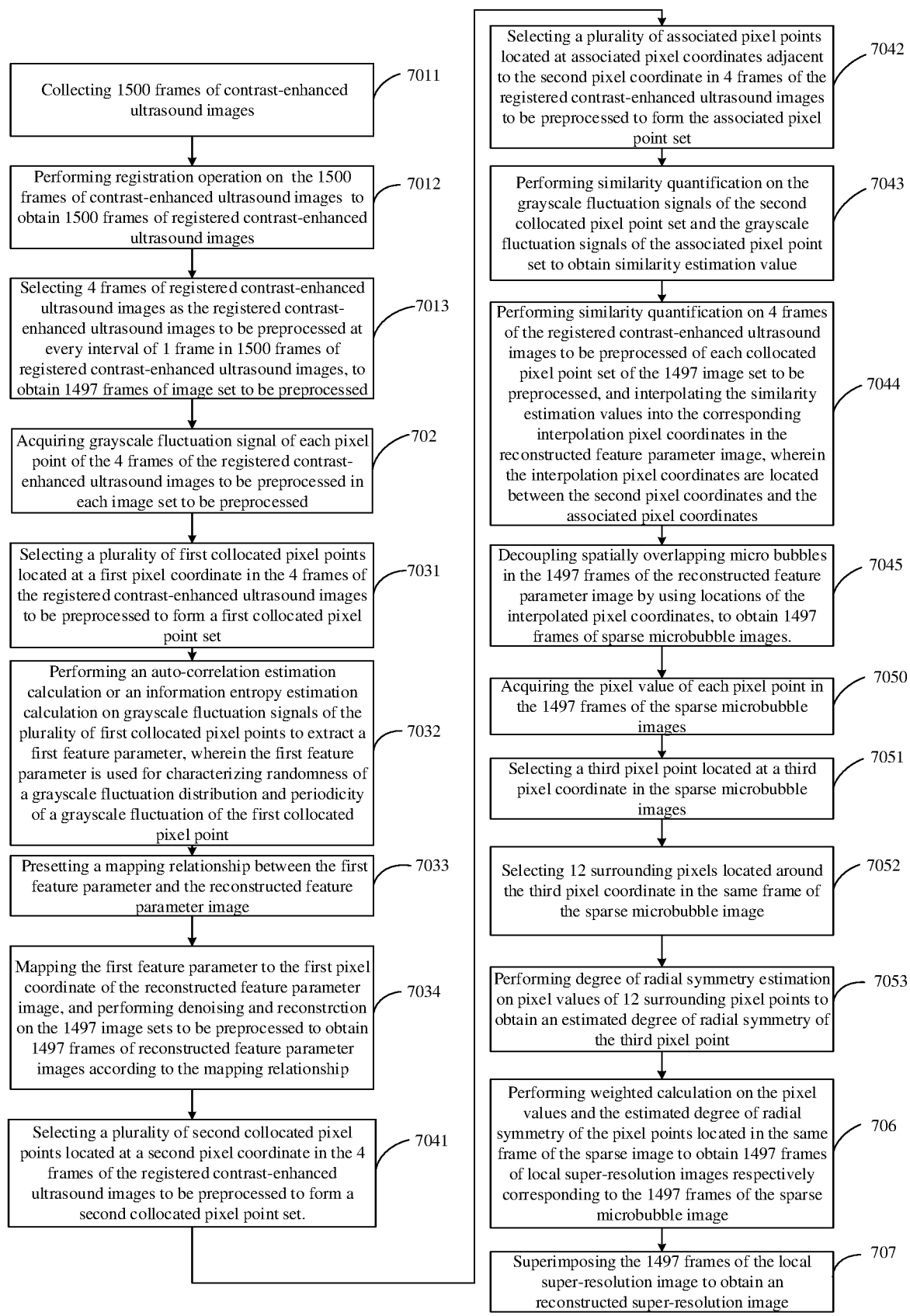
FIG. 7 is a flowchart of a super-resolution reconstruction preprocessing method of contrast-enhanced ultrasound images of a New Zealand white rabbit lower extremity bicep muscle according to an embodiment of the present application.

FIG. 7 is a flowchart of a super-resolution reconstruction preprocessing method of a contrast-enhanced ultrasound image of a New Zealand white rabbit's lower extremity bicep muscle according to an embodiment of the present application, wherein, N=1500, W+1=4, G=3.

1500 frames of contrast-enhanced ultrasound images of the New Zealand white rabbit's lower extremity bicep muscle are collected (as shown in step 7011 in FIG. 7). Contrast-enhanced ultrasound images is collected, and 1500 frames of the contrast-enhanced ultrasound images are acquired. The 1500 frames of the contrast-enhanced ultrasound images are registered to suppress image changes caused by probes and tissue motion to obtain 1500 frames of the registered contrast-enhanced ultrasound images (as shown in step 7012 in FIG. 7). The duration of the time window is selected as 4 frames of the contrast-enhanced ultrasound images, in the 1500 frames of the registered contrast-enhanced ultrasound images, 4 frames of the registered contrast-enhanced ultrasound images are selected as the registered contrast-enhanced ultrasound images to be preprocessed at every interval of 1 frame. And 1497 image set to be preprocessed are obtained (as shown in step 7013 in FIG. 7). The grayscale fluctuation signal of each pixel point of the 4 frames of the registered contrast-enhanced ultrasound images to be preprocessed in each image set to be preprocessed is obtained (as shown in step 702 in FIG. 7). By performing an auto-correlation estimation calculation or an information entropy estimation calculation on the grayscale fluctuation signals of each the collocated pixel point set of the 4 frames of the registered contrast-enhanced ultrasound images to be preprocessed (as shown in step 7031 in FIG. 7), a first feature parameter corresponding to each the collocated pixel point set is extracted (as shown in step 7032 in FIG. 7). According to the mapping relationship between the extracted first feature parameter and the reconstructed feature parameter image (as shown in step 7033 in FIG. 7), the reconstructed feature parameter image with the microbubble signal enhanced and the background or the noise signal weakened may be reconstructed (as shown in step 7034 in FIG. 7). Each pixel coordinate of the 4 frames of the registered contrast-enhanced ultrasound images to be preprocessed of the 1497 image sets to be preprocessed is traversed, and the 1497 image sets are denoised and reconstructed to obtain 1497 frames of the reconstructed feature parameter images with improved signal-to-noise ratio and signal-to-background ratio, realizing removal of most of the background and noise interference.

The grayscale fluctuation signals of each collocated pixel point set of the 4 frames of the registered contrast-enhanced ultrasound images to be preprocessed and the 4 associated pixel point sets adjacent to each collocated pixel point set are quantitatively calculated (as shown in step 7041 and step 7042 in FIG. 7), through a cross-entropy estimation or a cross-correlation estimation, thereby the similarity of the two signals becomes a more intuitive similarity estimation (as shown in step 7043 in FIG. 7). Each pixel coordinate of the 4 frames of the registered contrast-enhanced ultrasound images to be preprocessed is traversed, and the similarity estimation values of each the collocated pixel point set and the four associated pixel point sets are obtained. The similarity estimation value is interpolated into the corresponding interpolation pixel coordinate in the reconstructed feature parameter image (as shown in step 7044 in FIG. 7), so that the intuitive similarity estimation value is presented between each pixel in the reconstructed feature parameter image, and the overlapping microbubbles in the reconstructed feature parameter image are spatially decoupled to obtain the sparse microbubble image (as shown in step 7045 in FIG. 7). By using the estimation values of the collocated pixel points and the associated pixel points in the 4 frames of the registered contrast-enhanced ultrasound images to be preprocessed in each of the 1497 frames of the image set to be preprocessed, the 1497 frames of the reconstructed feature parameter images are interpolated, and the 1497 frames of the overlapping microbubbles in the reconstructed feature parameter image are spatially decoupled to obtain the 1497 frames of the sparse microbubble images.

The pixel value of each pixel point in each frame of the 1497 sparse microbubble images is obtained (as shown in step 7050 in FIG. 7). The degree of radial symmetry estimation is performed on the pixel values of the 12 surrounding pixel points corresponding to the pixel point in the same frame of the sparse microbubble image through the degree of radial symmetry estimation to obtain the estimated degree of radial symmetry of the pixel point (as shown in step 7051, step 7052, and step 7053 in FIG. 7). In each frame of the sparse microbubble image, by performing weighted calculation on the pixel values and the estimated degree of radial symmetry of each the pixel points traversed in the plurality of sparse microbubble image, the microbubble trajectory skeleton along the microbubble moving direction in each frame of the sparse microbubble image becomes clearer, therefore the deformation information of the microbubble is retained through the enhanced trajectory skeleton of the microbubble in each frame of the sparse microbubble image, the track information of the microbubble along the moving direction is retained, and local super-resolution images are obtained. (as shown in step 706 in FIG. 7). 1497 frames of the local super-resolution image are obtained and are superimposed to form a complete ultrasound super-resolution reconstructed image of the microvasculature (as shown in step 707 in FIG. 7).

Based on the fluctuation characteristic of the grayscale fluctuation signal of the microbubble in the time window, the application not only effectively filters out background or noise signal, and makes the microbubble signal significantly highlighted, but also realizes the efficient decoupling of the spatial overlapping microbubbles, thus the super-resolution accuracy is greatly improved.

Exemplary Super-Resolution Reconstruction Preprocessing Device

Figure 8:
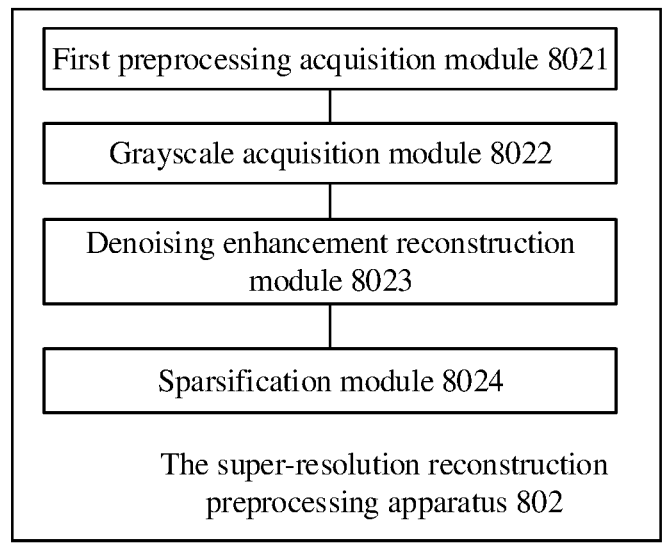
FIG. 8 is a schematic diagram of a super-resolution reconstruction preprocessing device of contrast-enhanced ultrasound images according to an embodiment of the present application.

FIG. 8 is a schematic diagram of a super-resolution reconstruction preprocessing device of contrast-enhanced ultrasound images according to an embodiment of the present application. As shown in FIG. 8, the super-resolution reconstruction preprocessing apparatus 802 includes: a first preprocessing acquisition module 8021, configured to acquire an image set to be preprocessed, the image set to be preprocessed including a plurality of frames of registered contrast-enhanced ultrasound images to be preprocessed; a grayscale acquisition module 8022, configured to acquire grayscale fluctuation signals of a pixel point in the registered contrast-enhanced ultrasound images to be preprocessed; a denoising enhancement reconstruction module 8023, configured to obtain grayscale fluctuation signals of pixel points in the registered contrast-enhanced ultrasound images to be preprocessed, and to perform denoising and reconstruction operation on the collocated pixel point set to be preprocessed based on grayscale fluctuation signals of collocated pixel point sets to obtain a reconstructed feature parameter image, the collocated pixel point set including a plurality of collocated pixel points located at a same pixel coordinate in different frames of the registered contrast-enhanced ultrasound images to be preprocessed; and a sparsification module 8024, configured to, based on the grayscale fluctuation signals of the collocated pixel point set and a grayscale fluctuation signals of an associated pixel point set associated with the collocated pixel point set, perform interpolation calculation on the reconstructed feature parameter image to obtain a sparse microbubble image, the associated pixel point set including a plurality of associated pixel points adjacent to the collocated pixel point in a same frame of the registered contrast-enhanced ultrasound images to be preprocessed and located at a same pixel coordinate in different frames of the registered contrast-enhanced ultrasound images to be preprocessed.

In the embodiment of the present application, by the denoising enhancement reconstruction module the grayscale fluctuation signals of the collocated pixel point set is analyzed, microbubble signals of the image to be preprocessed are distinguished from a noise signal or a background signal, a signal-to-noise ratio and a signal-to-background ratio are improved, and the reconstructed feature parameter image with enhanced microbubble signals and weakened background-noise signals. By the sparse module, the similarity of the grayscale fluctuation signals of the collocated pixel point set and the grayscale fluctuation signals of the associated pixel point set associated with the collocated pixel point set is calculated, the interpolation is made in the reconstructed feature parameter image to separate different microbubbles, so that spatial decoupling of overlapping microbubbles is realized, and influence of strong noise and high concentration microbubbles on reconstruction is effectively reduced.

In an embodiment, the grayscale fluctuation signal is a kind of signal formed by arranging pixel values of the pixel points in time sequence, and the grayscale fluctuation signals of the collocated pixel point set is a kind of one-dimensional signal formed by arranging pixel values of the plurality of collocated pixel points in the collocated pixel point set in time sequence.

Figure 9:
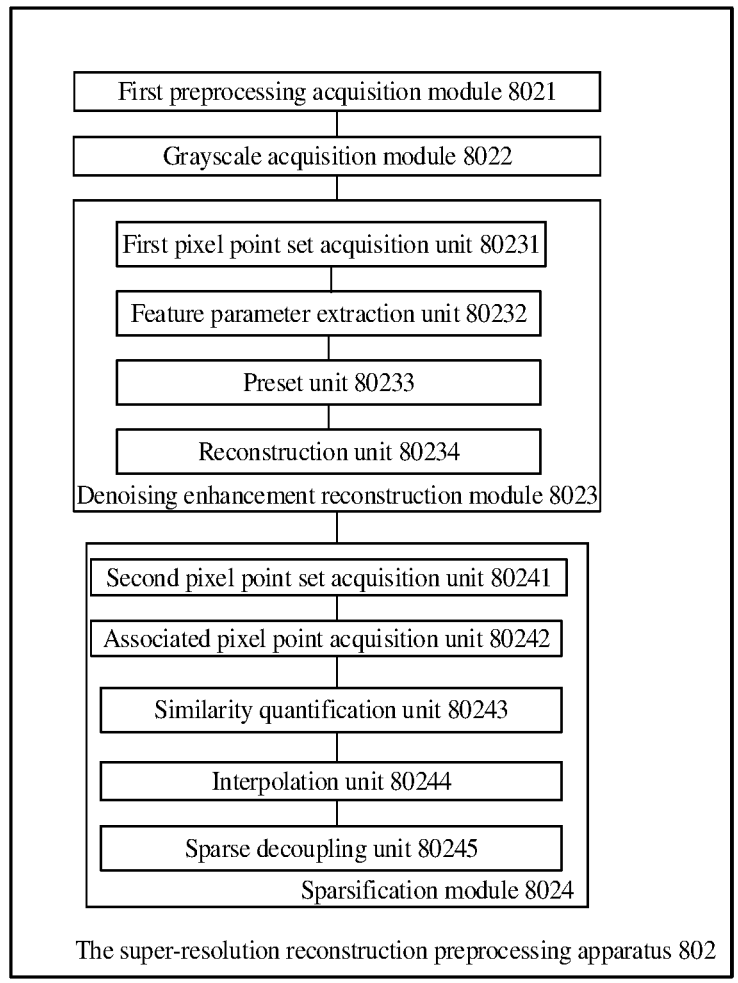
FIG. 9 is a schematic diagram of a super-resolution reconstruction preprocessing device of contrast-enhanced ultrasound images according to an embodiment of the present application.

FIG. 9 is a schematic diagram of a super-resolution reconstruction preprocessing device of contrast-enhanced ultrasound images according to an embodiment of the present application. As shown in FIG. 9, the denoising enhancement reconstruction module 8023 further includes: a first pixel point set acquisition unit 80231, configured to select a plurality of first collocated pixel points located at a first pixel coordinate in the plurality of frames of the registered contrast-enhanced ultrasound images to be preprocessed to form a first collocated pixel point set; a feature parameter extraction unit 80232, configured to perform feature estimation extraction operation on the grayscale fluctuation signals of the plurality of first collocated pixel points to obtain a first feature parameter, the first feature parameter being used for characterizing randomness and periodicity of a grayscale fluctuation distribution of the first collocated pixel point; a preset unit 80233, configured to preset a mapping relationship between the first feature parameter and a reconstructed feature parameter image; and a reconstruction unit 80234, configured to map the first feature parameter to the first pixel coordinate of a feature parameter image to be reconstructed to obtain the reconstructed feature parameter image according to the mapping relationship.

In an embodiment, methods of feature estimation extraction operation include: an auto-correlation estimation calculation or an information entropy estimation calculation.

In an embodiment, as shown in FIG. 9, the sparsification module 8024 includes: a second pixel point set acquisition unit 80241, configured to select a plurality of second collocated pixel points located at a second pixel coordinate in the plurality of frames of the registered contrast-enhanced ultrasound images to be preprocessed to form a second collocated pixel point set; an associated pixel point acquisition unit 80242, configured to select a plurality of associated pixel points located at associated pixel coordinates adjacent to the second pixel coordinate in the plurality of frames of the registered contrast-enhanced ultrasound images to be preprocessed to form an associated pixel point set; a similarity quantification unit 80243, configured to perform similarity quantification on the grayscale fluctuation signals of the second collocated pixel point set and the grayscale fluctuation signals of the associated pixel point set to obtain similarity estimation values; an interpolation unit 80244, configured to interpolate the similarity estimation values into the corresponding interpolation pixel coordinates in the reconstructed feature parameter image, the interpolation pixel coordinates being located between the second pixel coordinates and the associated pixel coordinates; and a sparse decoupling unit 80245, configured to decouple spatially overlapping microbubbles in the reconstructed feature parameter image using locations of the interpolated pixel coordinates to obtain the sparse microbubble image.

In an embodiment, methods of similarity quantification include: a cross-entropy estimation or a cross-correlation estimation.

In an embodiment, a quantity of the associated pixel point set is 4.

Exemplary Super-Resolution Reconstruction Apparatus

Figure 10:
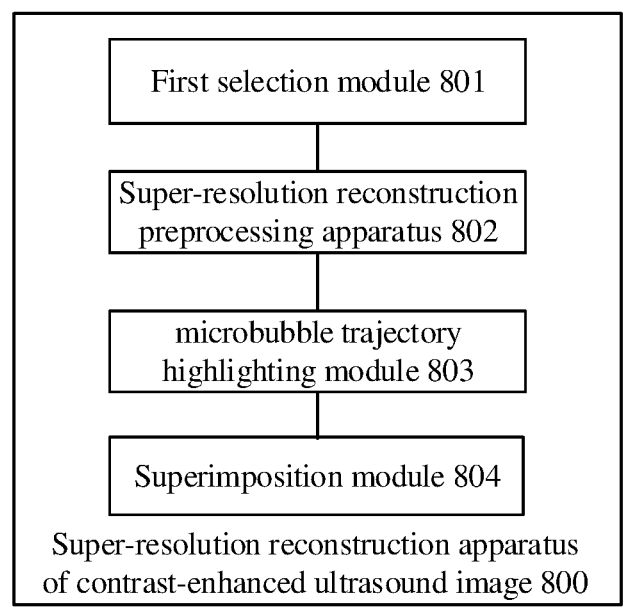
FIG. 10 is a schematic diagram of a super-resolution reconstruction apparatus of contrast-enhanced ultrasound images according to an embodiment of the present application.

FIG. 10 is a schematic diagram of a super-resolution reconstruction apparatus of contrast-enhanced ultrasound images according to an embodiment of the present application. As shown in FIG. 10, the super-resolution reconstruction apparatus 800 includes: a first selection module 801, configured to select at least one image set to be preprocessed from contrast-enhanced ultrasound images; a super-resolution reconstruction preprocessing apparatus 802, configured to perform preprocessing operation on at least one image set to be preprocessed respectively to obtain at least one frame of sparse microbubble image, a method of the preprocessing adopting the super-resolution reconstruction preprocessing method according to any one of the above-mentioned the super-resolution reconstruction preprocessing methods; an microbubble trajectory highlighting module 803, configured to acquire pixel values and estimated degree of radial symmetry of pixel points in the sparse microbubble image and perform weighted calculation on the pixel values and the estimated degree of radial symmetry of the pixel points located in the same frame of the sparse microbubble image to obtain at least one local super-resolution image respectively corresponding to at least one frame of the sparse microbubble image; and a superimposition module 804, configured to superimpose at least one frame of the local super-resolution image to obtain a reconstructed super-resolution image.

In the embodiment of the application, by the super-resolution reconstruction preprocessing apparatus performing preprocessing operation on at least one image set to be preprocessed, influence of high concentration microbubbles and strong noise on an accuracy of super-resolution imaging may be effectively reduced. By the microbubble trajectory highlighting module performing weighted calculation on the pixel values and the estimated degree of radial symmetry of the pixel points located in each frame of the sparse microbubble image, point spread function of the microbubbles is slimmed along the moving direction of the microbubble, therefore the deformation information of the microbubble is retained through the enhanced trajectory skeleton of the microbubble in each frame of the sparse microbubble image, the track information of the microbubble along the moving direction is retained, and local super-resolution images are obtained. By superimposition module, the local super-resolution images are finally integrated into the complete ultrasound super-resolution reconstruction image of microvasculature. Different from traditional ultrasound localization microscopy strategy, the reconstruction apparatus retains the skeleton of microbubble trajectory along the moving direction of microbubble in a non-localization-based way. Thereby spatial resolution and reconstruction speed of the super-resolution reconstructed image are greatly improved.

Figure 11:
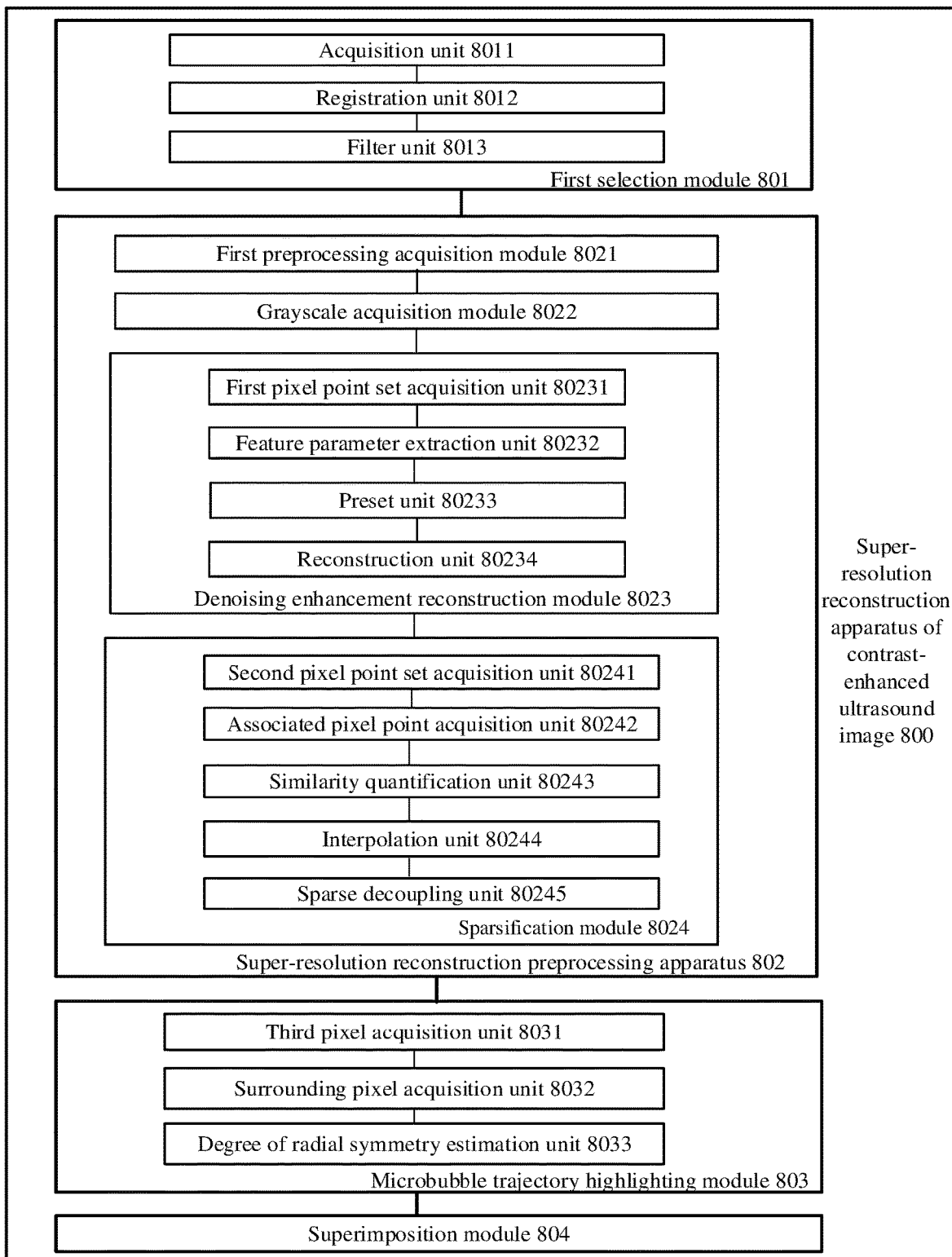
FIG. 11 is a schematic diagram of a super-resolution reconstruction apparatus of contrast-enhanced ultrasound images according to an embodiment of the present application.

FIG. 11 is a schematic structural diagram of a super-resolution reconstruction apparatus of contrast-enhanced ultrasound images according to an embodiment of the present application. As shown in FIG. 11, the microbubble trajectory highlighting module 803 includes: a third pixel acquisition unit 8031, configured to select a third pixel point located at a third pixel coordinate in a sparse microbubble image; a surrounding pixel acquisition unit 8032, configured to select a plurality of surrounding pixels located around the third pixel coordinate in a same frame of the sparse microbubble image; and a degree of radial symmetry estimation unit 8033, configured to perform degree of radial symmetry estimation on pixel values of the plurality of surrounding pixel points to obtain an estimated degree of radial symmetry of the third pixel point.

In an embodiment, as shown in FIG. 11, the first selection module 801 further includes: an acquisition unit 8011, configured to acquire a plurality of frames of contrast-enhanced ultrasound images; an registration unit 8012, configured to perform registration operation on the plurality of frames of the contrast-enhanced ultrasound images to suppress interference of tissue motion to obtain a plurality of frames of the registered contrast-enhanced ultrasound images; and a filter unit 8013, configured to select a second preset quantity of frames of the registered contrast-enhanced ultrasound images at a interval of a first preset quantity of frames among the plurality of frames of the registered contrast-enhanced ultrasound images as the registered contrast-enhanced ultrasound images to be preprocessed, to obtain at least one image set to be preprocessed.

In an embodiment, the first preset quantity is negatively correlated with blood flow velocity; and the second preset quantity is negatively correlated with the blood flow velocity.

In an embodiment, the first preset quantity is positively correlated with imaging frame rate; and the second preset quantity is positively correlated with the imaging frame rate.

In an embodiment, the first preset quantity is 1; and the second preset quantity is 4.

The specific functions and operations of the preprocessing device in the super-resolution reconstruction apparatus of contrast-enhanced ultrasound images have been described in detail above with reference to the super-resolution reconstruction preprocessing methods shown in FIG. 1 to FIG. 3; the specific functions and operations of other modules in the reconstruction apparatus are described in detail in the super-resolution reconstruction methods described in FIG. 4 to FIG. 6, therefore, the repeated description thereof will be omitted here.

It should be noted that the super-resolution reconstruction preprocessing device 800 of contrast-enhanced ultrasound images according to embodiments of the present application may be integrated into the electronic device 1200 as a software module and/or a hardware module, in other words, the electronic device 1200 may include super-resolution reconstruction preprocessing device 800 of a contrast-enhanced ultrasound image. For example, the super-resolution reconstruction apparatus 800 of contrast-enhanced ultrasound images may be a software module in the operating system of the electronic device 1200, or may be an application program developed for it; of course, the super-resolution reconstruction preprocessing device 800 of a contrast-enhanced ultrasound image may also be one of many hardware modules of the electronic device 1200.

In another embodiment of the present application, the super-resolution reconstruction apparatus 800 of contrast-enhanced ultrasound images and the electronic device 1200 may also be separate devices (e.g. a server), and the super-resolution reconstruction apparatus 800 of contrast-enhanced ultrasound images may be connected to the electronic device 1200 through wired and/or wireless network with the interaction information transmitted according to the agreed data format.

Exemplary Electronic Device

Figure 12:
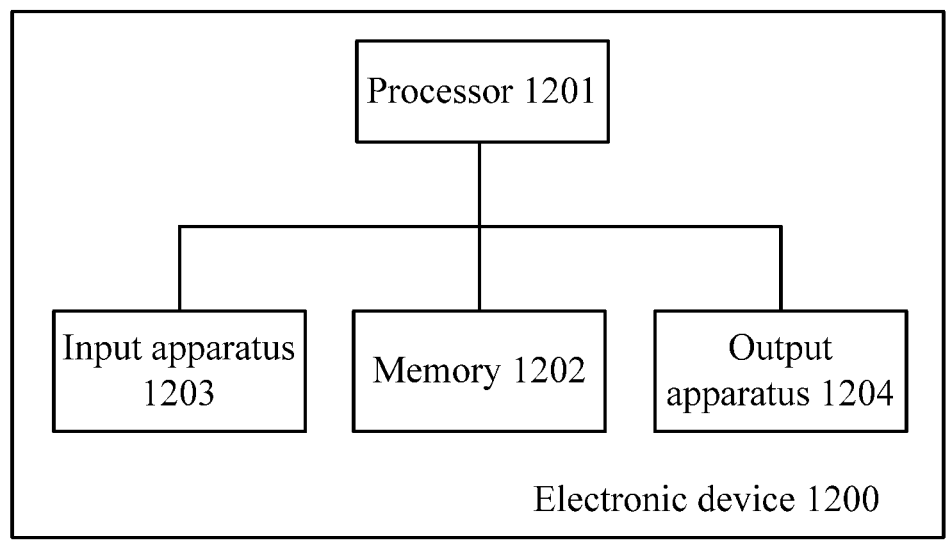
FIG. 12 is a schematic structural diagram of an electronic device according to an embodiment of the present application.

FIG. 12 is a schematic structural diagram of an electronic device according to an embodiment of the present application. As shown in FIG. 12, the electronic device 1200 includes one or more processors 1201, a memory 1202, and computer program instructions stored in memory 1202. The computer program instructions, when executed by the processor 1201, cause the processor 1201 to perform the super-resolution reconstruction preprocessing method of any of the above-mentioned embodiments or the super-resolution reconstruction method of any of the above-mentioned embodiments.

The processor 1201 may be a Central Processing Unit (CPU) or another form of processing unit with data processing capability and/or instruction execution capability, and may control another component in the electronic device to perform an expected function.

The memory 1202 may include one or more computer program products, which may include various forms of computer-readable storage media, such as a volatile memory and/or non-volatile memory. The volatile memory may include, for example, a Random Access Memory (RAM) and/or a cache (cache). The non-volatile memory may include, for example, a Read-Only Memory (ROM), a hard disk, and a flash memory. The computer readable storage medium may store one or more computer program instructions, and the processor 1201 may execute the program instructions to realize the steps of the super-resolution reconstruction preprocessing method or the super-resolution reconstruction method of any of the above-mentioned embodiments of the present application and/or other expected functions. Information such as light intensity, compensation light intensity, location of filters, etc. may also be stored in the computer readable storage medium.

In an embodiment, the electronic device 1200 may further include: an input device 1203 and an output device 1204, these components being interconnected by using a bus system and/or another form of connection mechanism (not shown in FIG. 12).

In addition, the input device 1203 may also include, for example, a keyboard, a mouse, a microphone and so on.

The output device 1204 may output various information to the outside. The output device 1204 may include, for example, a display, a speaker, a printer, a communication network and a remote output device connected to it, and so on.

Certainly, for simplicity, only some of the components related to the present application in the electronic device 1200 are shown in FIG. 12, and components such as a bus, and an input/output interface are omitted. In addition, the electronic device 1200 may further include any other suitable components depending on specific application cases.

Exemplary Computer Program Product and Computer Readable Storage Medium

In addition to the above-mentioned methods and devices, an embodiment of the present application may also be a computer program product that includes computer program instructions. The computer program instructions, when executed by the processor, cause the processor to perform the steps in the super-resolution reconstruction preprocessing method of any of the above-mentioned embodiments or the super-resolution reconstruction method of any of the above-mentioned embodiments.

The computer program product may write program code for performing the operations of the embodiments of the present application in any combination of one or more programming languages, and the programming languages include object-oriented programming languages such as Java and C++, and further include conventional procedural programming languages such as "C" or similar programming languages. The program code may be executed entirely on a user computing device, partly on a user device, as a stand-alone software package, partly on a user computing device while partly on a remote computing device, or entirely on a remote computing device or a server.

In addition, an embodiment of the present application may also be a non-transitory computer readable storage medium, where the non-transitory computer readable storage medium stores computer program instructions. When the computer program instructions are run by a processor, the processor is enabled to perform the steps of the super-resolution reconstruction preprocessing method or the steps of the super-resolution reconstruction method according to the embodiments of the present application described in the "Exemplary Preprocessing Method" part of this specification, or in the "Exemplary Reconstruction Method" part of this specification.

The computer readable storage medium may use any combination of one or more readable mediums. The readable medium may be a readable signal medium or a readable storage medium. The readable storage medium may include, for example, but not limited to, an electronic, magnetic, optical, electromagnetic, infrared, or semiconductor system, apparatus, or means, or any combination of the above. More specific examples (a non-exhaustive list) of the readable storage medium include: an electrical connection having one or more wires, a portable computer disk, a hard disk, a Random Access Memory (RAM), a Read-Only Memory (ROM), an Erasable Programmable Read-Only Memory (EPROM or a flash memory), an optical fiber, a portable Compact Disk Read-Only Memory (CD-ROM), an optical storage means, a magnetic storage means, or any suitable combination of the above.

The basic principles of the present application are described with reference to specific embodiments. However, it may be noted that the merits, advantages, effects, and the like mentioned in the present application are merely examples but not limitations, and it cannot be considered that these merits, advantages, effects, and the like are essential to the embodiments of the present application. In addition, the specific details disclosed above are intended only for the purpose of illustration and convenience of understanding, and are not limited thereto, and are not intended to limit the present application to the specific details described above.

The block diagrams of components, apparatuses, devices and systems in the present application are merely illustrative examples and are not intended to require or imply that connections, arrangements and configurations must be performed in the manner shown in the block diagrams. As will be recognized by those skilled in the art, these components, apparatuses, devices and systems can be connected, arranged and configured in any manner. Terms such as "comprise", "include", "have" are open words, meaning "include but not limited to", and they can be used interchangeably. Terms "or" and "and" used herein refer to "and/or", and they can be used interchangeably unless the context expressly indicates otherwise. Term "such as" used herein refers to "such as but not limited to" and they can be used interchangeably.

It may also be noted that, in the apparatuses, devices and methods of the present application, components or steps can be decomposed and/or recombined. These decompositions and/or recombination shall be considered as equivalent solutions of the present application.

The above-mentioned descriptions of the disclosed aspects are provided to enable any person skilled in the art to make or use the present application. Modifications to these aspects are very obvious to those skilled in the art and the general principles defined herein can be applied to other aspects without departing from the scope of the present application. Therefore, the present application is not intended to be limited to the aspects shown herein, but to the widest extent consistent with the principles and novel features disclosed herein.

The above description has been presented for the purposes of illustration and description. Furthermore, this description is not intended to limit the embodiments of the present application to the forms disclosed herein. Although a number of example aspects and embodiments have been discussed above, those skilled in the art will recognize certain variations, modifications, changes, additions and sub-combinations thereof.

The above are only the implementation manners of the present application, and the description is relatively specific and detailed, but it should not be understood as a limitation to the scope of the present application. It may be pointed out that for those skilled in the art, without departing from the concept of the present application, several modifications and improvements may be made, and these all fall within the protection scope of this application.

What is claimed is:

1. A super-resolution reconstruction preprocessing method of contrast-enhanced ultrasound images, comprising:
   acquiring an image set to be preprocessed, the image set to be preprocessed comprising a plurality of frames of registered contrast-enhanced ultrasound images to be preprocessed;
   acquiring grayscale fluctuation signals of pixel points in the plurality of registered contrast-enhanced ultrasound images to be preprocessed;
   performing denoising and reconstruction operation on the image set to be preprocessed to obtain a reconstructed feature parameter image, based on grayscale fluctuation signals of a collocated pixel point set, the collocated pixel point set comprising a plurality of collocated pixel points located at a same pixel coordinate in different frames of registered contrast-enhanced ultrasound images to be preprocessed; and
   performing interpolation calculation on the reconstructed feature parameter image to obtain a sparse microbubble image, based on the grayscale fluctuation signals of the collocated pixel point set and grayscale fluctuation signals of an associated pixel point set associated with the collocated pixel point set, the associated pixel point set comprising a plurality of associated pixel points, the plurality of associated pixel points being adjacent to the collocated pixel point in a same frame of the registered contrast-enhanced ultrasound image to be preprocessed and being located at a same pixel coordinate in different frames of the registered contrast-enhanced ultrasound images to be preprocessed.

2. The super-resolution reconstruction preprocessing method of claim 1, wherein the grayscale fluctuation signals are signals formed by arranging pixel values of the pixel points arranged in time sequence, and the grayscale fluctuation signals of the collocated pixel point set are one-dimensional signals formed by arranging pixel values of the plurality of collocated pixel points in the collocated pixel point set in time sequence.

3. The super-resolution reconstruction preprocessing method of claim 1, wherein the performing denoising and reconstruction operation on the image set to be preprocessed to obtain a reconstructed feature parameter image, based on grayscale fluctuation signals of a collocated pixel point set comprises:
   selecting a plurality of first collocated pixel points located at a first pixel coordinate in the plurality of frames of registered contrast-enhanced ultrasound images to be preprocessed to form a first collocated pixel point set;
   performing feature estimation extraction operation on grayscale fluctuation signals of the plurality of first collocated pixel points to obtain a first feature parameter, the first feature parameter being used for characterizing randomness of a grayscale fluctuation distribution and periodicity of a grayscale fluctuation of the first collocated pixel point;
   presetting a mapping relationship between the first feature parameter and the reconstructed feature parameter image; and
   mapping the first feature parameter to the first pixel coordinate of a feature parameter image to be reconstructed to obtain the reconstructed feature parameter image according to the mapping relationship.

4. The super-resolution reconstruction preprocessing method of claim 3, wherein a method of the feature estimation extraction operation comprises: auto-correlation estimation calculation or information entropy estimation calculation.

5. The super-resolution reconstruction preprocessing method of claim 3, wherein the larger a value of the first feature parameter is, the higher a gray value of a pixel point corresponding to the first feature parameter in the reconstructed feature parameter image is.

6. The super-resolution reconstruction preprocessing method of claim 1, wherein the performing interpolation calculation on the reconstructed feature parameter image to obtain a sparse microbubble image, based on the grayscale fluctuation signals of the collocated pixel point set and grayscale fluctuation signals of an associated pixel point set associated with the collocated pixel point set, comprises:

selecting a plurality of second collocated pixel points located at a second pixel coordinate in the plurality of frames of the registered contrast-enhanced ultrasound images to be preprocessed to form a second collocated pixel point set;

selecting a plurality of associated pixel points located at associated pixel coordinates adjacent to the second pixel coordinate in the plurality of frames of the registered contrast-enhanced ultrasound images to be preprocessed to form the associated pixel point set;

performing similarity quantification on the grayscale fluctuation signals of the second collocated pixel point set and the grayscale fluctuation signals of the associated pixel point set to obtain similarity estimation values;

interpolating the similarity estimation values into corresponding interpolation pixel coordinates in the reconstructed feature parameter image, the interpolation pixel coordinates being located between the second pixel coordinates and the associated pixel coordinates; and decoupling spatially overlapping microbubbles in the reconstructed feature parameter image to obtain the sparse microbubble image, by using locations of the interpolated pixel coordinates.

7. The super-resolution reconstruction preprocessing method of claim 6, wherein a method of similarity quantification comprises: cross-entropy estimation or cross-correlation estimation.

8. The super-resolution reconstruction preprocessing method of claim 1, wherein a quantity of the associated pixel point set is 4.

9. A super-resolution reconstruction method of a contrast-enhanced ultrasound image, comprising:

selecting at least one image set to be preprocessed from contrast-enhanced ultrasound images;

performing preprocessing operation on at least one image set to be preprocessed respectively to obtain at least one frame of sparse microbubble image, a method of the preprocessing operation adopting the super-resolution reconstruction preprocessing method according to claim 1;

acquiring pixel values and estimated degree of radial symmetry of pixel points in the sparse microbubble image;

performing weighted calculation on the pixel values and the estimated degree of radial symmetry of the pixel points located in the same frame of the sparse microbubble image to obtain at least one frame of local super-resolution image respectively corresponding to the at least one frame of sparse microbubble image; and superimposing at least one frame of the local super-resolution image to obtain a reconstructed super-resolution image.

10. The super-resolution reconstruction method of claim 9, wherein the acquiring the estimated degree of radial symmetry of the pixel points in the sparse microbubble image comprises:

selecting a third pixel point located at a third pixel coordinate in the sparse microbubble image;

selecting a plurality of surrounding pixels located around the third pixel coordinate in a same frame of sparse microbubble image; and performing degree of radial symmetry estimation on pixel values of the plurality of surrounding pixel points to obtain an estimated degree of radial symmetry of the third pixel point.

11. The super-resolution reconstruction method of claim 10, wherein a quantity of the surrounding pixel points is 12.

12. The super-resolution reconstruction method of claim 9, wherein the selecting at least one image set to be preprocessed from contrast-enhanced ultrasound images comprises:

acquiring a plurality of frames of contrast-enhanced ultrasound images;

performing registration operation on the plurality of frames of contrast-enhanced ultrasound images to suppress interference of tissue motion, to obtain a plurality of frames of registered contrast-enhanced ultrasound images; and selecting a second preset quantity of frames of registered contrast-enhanced ultrasound images at an interval of a first preset quantity among the plurality of frames of registered contrast-enhanced ultrasound images as registered contrast-enhanced ultrasound images to be preprocessed, to obtain the at least one image set to be preprocessed.

13. The super-resolution reconstruction method of claim 12, wherein the first preset quantity is negatively correlated with a blood flow velocity; and the second preset quantity is negatively correlated with the blood flow velocity.

14. The super-resolution reconstruction method of claim 12, wherein the first preset quantity is positively correlated with imaging frame rate; and the second preset quantity is positively correlated with the imaging frame rate.

15. The super-resolution reconstruction method of claim 12, wherein the first preset quantity is 1, and the second preset quantity is 4.

16. An electronic device, comprising:
a processor; and
a memory, wherein a computer program instruction is stored in the memory and the processor is configured to execute the super-resolution reconstruction preprocessing method according to claim 1 during the execution of the computer program instruction by the processor.

17. An electronic device, comprising:
a processor; and
a memory, wherein a computer program instruction is stored in the memory and the processor is configured to execute the super-resolution reconstruction method according to claim 9 during the execution of the computer program instruction by the processor.

18. A non-transitory computer readable storage medium, wherein a computer program instruction is stored in the non-transitory computer readable storage medium and a processor is configured to execute the super-resolution reconstruction preprocessing method according to claim 1 during the execution of the computer program instruction by the processor.

19. A non-transitory computer readable storage medium, wherein a computer program instruction is stored in the non-transitory computer readable storage medium and a processor is configured to execute the super-resolution reconstruction method according to claim 9 during the execution of the computer program instruction by the processor.

* * * * *